(12) United States Patent
Chamdani et al.

(10) Patent No.: US 11,238,636 B2
(45) Date of Patent: *Feb. 1, 2022

(54) METHOD AND APPARATUS FOR SPORT-SPECIFIC TRAINING WITH CAPTURED BODY MOTIONS

(71) Applicant: TuringSense Inc., Santa Clara, CA (US)

(72) Inventors: Joseph I. Chamdani, Santa Clara, CA (US); Pietro Garofalo, Forli (IT); Cecylia Wati, Hayward, CA (US); Limin He, Monte Sereno, CA (US)

(73) Assignee: Turingsense Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/202,345

(22) Filed: Mar. 16, 2021

(65) Prior Publication Data

US 2021/0201554 A1 Jul. 1, 2021

Related U.S. Application Data

(63) Continuation of application No. 16/827,331, filed on Mar. 23, 2020, now Pat. No. 10,950,025, which is a continuation of application No. 16/423,130, filed on May 27, 2019, now Pat. No. 10,672,173, which is a continuation of application No. 16/219,727, filed on Dec. 13, 2018, now Pat. No. 10,304,230, which is a continuation of application No. 15/271,205, filed on Sep. 20, 2016, now Pat. No. 10,157,488.

(60) Provisional application No. 62/221,502, filed on Sep. 21, 2015.

(51) Int. Cl.
*G06F 3/045* (2006.01)
*G06T 13/40* (2011.01)
*G06F 3/01* (2006.01)

(52) U.S. Cl.
CPC .............. *G06T 13/40* (2013.01); *G06F 3/011* (2013.01); *G06F 3/014* (2013.01); *G06F 3/017* (2013.01)

(58) Field of Classification Search
CPC .......... G06F 3/011; G06F 3/014; G06F 3/017; G06T 13/40; G06K 9/00523; G06K 9/00536; G06K 9/00671; G06K 9/00342; G16H 50/30; G16H 20/30; G09B 19/0038
See application file for complete search history.

(56) References Cited

U.S. PATENT DOCUMENTS 10,157,488 B2 * 12/2018 Chamdani .......... G06K 9/00342
10,304,230 B2 * 5/2019 Chamdani .......... G06K 9/00671
10,672,173 B2 * 6/2020 Chamdani ............... G06F 3/011

* cited by examiner

Primary Examiner — Vijay Shankar
(74) Attorney, Agent, or Firm — Joe Zheng

(57) ABSTRACT

Techniques for sport-specific training with captured body motions are described. A computing device is provided to receive sensing data wirelessly from a plurality of sensor modules respectively attached to different body parts of a user in accordance with a particular sport. The motion of the user per the received sensing data is derived. A corresponding 3D graphic environment pertaining to the sport is provided on a display to show reference motion performed by a reference chosen by the user with the derived motion performed by the user. Differences between the reference motion and the derived motion are highlighted or animated in the 3D graphic environment.

20 Claims, 35 Drawing Sheets

There are several options:

A) Align the sensor as much as possible with the bone and use a static posture as reference
 -- not applicable to all segments
 -- suffers from artifacts
B) Assume alignment with the gravity direction during a static posture
C) Estimate axes of rotation using functional movements and special algorithms
 -- required for non ball&socet joints

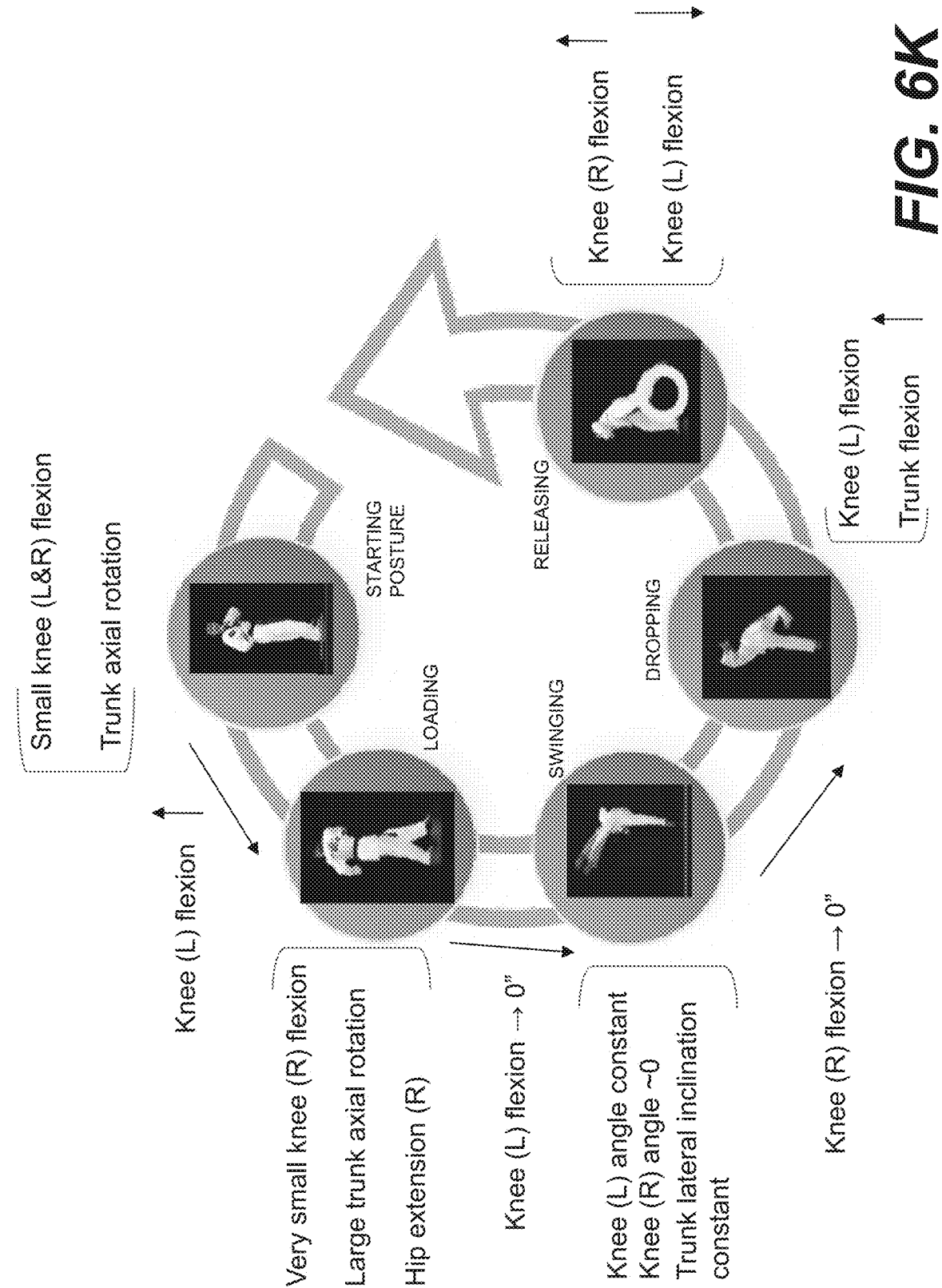

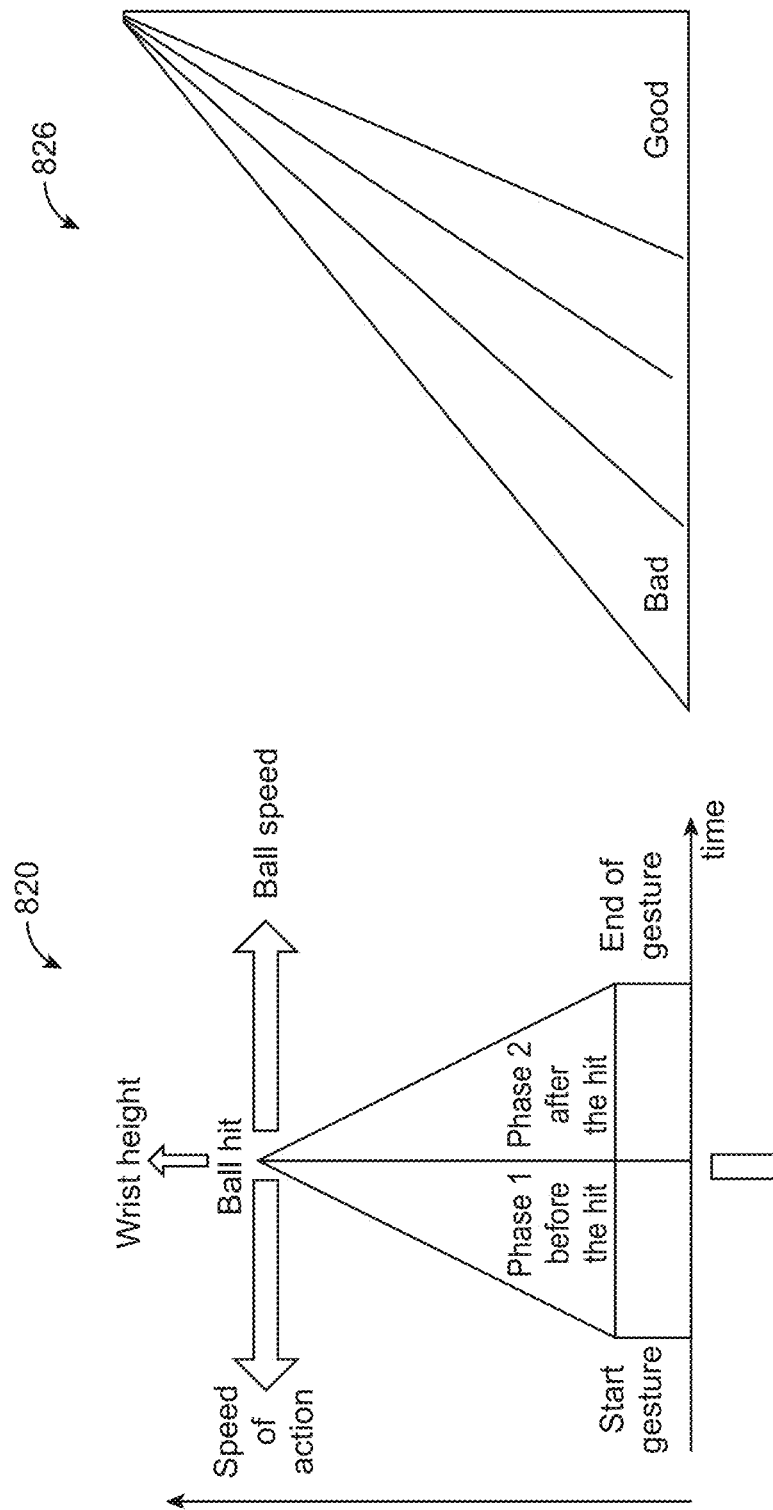

METHOD AND APPARATUS FOR SPORT-SPECIFIC TRAINING WITH CAPTURED BODY MOTIONS

CROSS-REFERENCE TO RELATED APPLICATION

This application is a continuation of U.S. application Ser. No. 16/827,331, now U.S. Pat. No. 10,950,025, which is a continuation of U.S. application Ser. No. 16/423,130, now U.S. Pat. No. 10,672,173, which is a continuation of U.S. application Ser. No. 16/219,727, now U.S. Pat. No. 10,304,230, which is a continuation of U.S. application Ser. No. 15/271,205, now U.S. Pat. No. 10,157,488, which claims the benefits of US provisional application No.: 62/221,502, entitled "SYSTEM AND METHOD FOR CAPTURING AND ANALYZING COMPLEX MOTIONS", filed on Sep. 21, 2015, which is hereby incorporated by reference for all purposes.

BACKGROUND OF THE INVENTION

1. Field of the Invention

The present invention relates generally to motion detections, and more particularly to methods and systems for analyzing complex motions, such as the movements by a person performing sports activities.

2. Related Art

Wearable technology is on the rise in personal and business use. For example, in sports and fitness, wearable technology has applications in monitoring and real-time feedback. The decreasing cost of processing power and other components is encouraging widespread adoption and availability. However, the known technology is limited in its ability to provide useful analysis and high-speed determination of motions captured by a set of sensing devices placed on different parts of a body.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In general, the present invention is related to capturing and analyzing complex motions made by a person performing activities. According to one aspect of the present invention, sensing devices or sensor modules are attached to different parts of a body. As a person makes moves, the sensor modules, each including at least one inertial sensor, producing sensing data that are locally received in one module in communication with an external device either remotely or locally. Relying on the resources on the external device, the combined sensing data received from these sensor modules are processed and analyzed to derive the motions made the person. Depending on implementation, the external device may be a mobile device, a server or a part of servers (a.k.a., cloud computing).

According to another aspect of the present invention, one of the sensor modules designated to receive sensing data from other sensor modules is referred to as a hub module while the remaining sensor modules are referred to as satellite modules. Accordingly, a wireless protocol for real-time low-latency streaming is provided and described for intercommunication between a hub module and each of its satellite modules with features including at least timestamp synchronization, clock-skew mitigation, packet retransmission, error correction, sensor data compression, star-network topology, tree-network topology, and/or auto-frequency hopping.

According to still another aspect of the present invention, a data process is provided using combination of gyroscope, accelerometer, magnetometer data with features to compensate for MEM (micro-electro-mechanical) sensor data drifts, integrate human biomechanical model as a close-loop control system, automatically detect and warn a user of magnetic interference/environment change, allow a user to do simple quick static-pose calibration with consistent joint angle accuracy, avoid sensor drifts in very high-speed motions, and compensate for missing sensor data.

According to still another aspect of the present invention, a process is provided to classify various motions (e.g., forehand, backhand, serve, volley, overhead, return of serve, slice in tennis strokes), stroke phases (ready pose, back swing, forward swing, ball contact, follow through, recovery), motion gesture recognition (e.g., foot hop, chest tap), footwork steps, ball contact location, kinetic chain and balance, weight transfer, head still, detect a "bad habit" motion symptom and intelligently guide a user for a fix or automated lesson.

According to still another aspect of the present invention, a cloud architecture, design, or implementation is provided with features to support real-time sensor data streaming from thousands of users simultaneously, compute-intensive sensor/motion processing with milliseconds latency, streaming back to a client device for 3D motion animation/analysis, synchronization of user metadata, motion library and session recordings, instant playback of current/previous recording, remote coaching/viewing/broadcast, and sharing one's motions with one or more other users.

According to still another aspect of the present invention, 3D graphics animation is provided with features to compare reference motion vs. actual motion having continuous and/or multi-pose motion, shadow train with imitation game, live on-court train with instant audio feedback, and materialize real movement of an object held in a user hand (e.g., tennis racquet).

According to still another aspect of the present invention, a motion library is provided with features to allow users to store reference motions trimmed from recorded motions, select a motion to setup a specific lesson and train on-court with instant audio feedback, select a motion to imitate in a shadow motion game, share a library with a group of users (e.g., tennis academy group), and immortalize and monetize motions of elite pros/users.

According to still another aspect of the present invention, a wearable system is architected for many applications involving motions, wherein the system is designed for analyzing complex motions by one or more persons in areas, such as, sports, AR/VR, healthcare, and etc. The system is applicable or modified uniquely for each target application. This application-oriented approach provides a more efficient and accurate design.

According to yet another aspect of the present invention, the system can be a camera-less, full-body motion capture and motion analysis product built specifically for a sport (e.g., tennis). A wireless and portable device provides instant biomechanics feedback for technique optimization and injury prevention. Scalable, cloud-based technology enables users to store and share session data in real-time with coaches, friends and family anywhere in the world via a mobile application (App), as well as compare a user's technique versus reference players (including pros) in a stored motion library.

The present invention may be implemented as a system, a part of a system, a method, a process or a product. Different embodiments may yield different advantages, benefits or objectives. It is believed that various implementations may lead to results that may not be achieved conventionally. According to one embodiment, the present invention is a system employing a plurality of motion modules attached to different parts of a human body, tracking of motions of different body segments. Each of the sensor modules includes at least one inertial sensor or integrated gyroscope, accelerometer, and magnetometer. Further each of the sensor modules includes a wireless transceiver so that the sensing data can be transported to a computing device to view the full motion of the person after the sensing data from some or all of the sensor modules is analyzed and integrated. With a properly designed App, a computing device allows playback of current and past recordings of the sensor data in 360-degree view with slow motion, zoom and etc. The system also allows for comparison with reference strokes in a motion library that is composed of pro players, user-added players, user's own reference strokes, etc. In addition, the system is provided for sharing session recordings with coaches, friends, and family and storing of historical sessions for years, and for real-time live remote coaching capabilities in any distant place. Optionally, the system is designed to perform various data analytics to get advanced insights and information about a user's motion to derive the techniques in a game the user is playing.

According to another embodiment, the present invention is a system for capturing motion performed by a user, the system comprises a plurality of sensor modules respectively attached to different parts of a body, at least one of the sensor modules acting as hub module and the rest of the sensor modules acting as satellite modules, and each of the sensor modules including a microcontroller, at least an inertial sensor and a transceiver for intercommunication with the hub module. The hub module further includes another transceiver for communicating with an external computing device, each of the sensor modules produces sensing data at a predefined frequency when a user makes moves, the sensing data from the satellite modules are received in the hub module and combined with the sensing data generated within the hub module to be transported wirelessly to the external device designed to derive the motion of the user performing activities and facilitate a comparison between the derived motion with stored motion to illustrate a difference between the motion made by the user and motion made by another person According to still another embodiment, the present invention is a method for capturing motion performed by a user, the method comprises: providing a plurality of sensor modules respectively attached to different parts of a body, where at least one of the sensor modules is designated as a hub module and the rest of the sensor modules are designated as satellite modules; establishing an intercommunication session between the hub module and each of the satellite modules to receive sensing data in the hub module from the satellite modules; generating sensing signals in each of the modules when the user performs certain activities, the sensing signals sampled at a predefined frequency; combining the received sensing data with sensing data generated in the hub module; transporting the combined sensing data from the hub module to an external computing device for processing, wherein the combined sensing data is analyzed to derive motion of a user performing activities; and comparing the derived motion with stored motion to illustrate a difference between the motion made by the user and motion made by another person.

According to yet another embodiment, the present invention is a method for communication between a hub module and a plurality of satellite modules, the method comprising: searching by the hub module each of the satellite modules per a list of the satellite modules in a first channel, wherein the list includes an identifier of each of the satellite modules; switching to a second channel by the hub module to continue searching each of the satellite modules per the list when one of the satellite modules is not responsive in the first channel, wherein each of the first and second channels is an inbound channel and paired with an outbound channel, there is at least one unused channel between a pair of inbound and outbound channels. The method further comprises encoding data packets based on an error correction coding scheme to reduce impact on neighboring data packets when one of the data packets is corrupted when being transported between the hub and one of the satellite modules.

There are many objects, features, and advantages in the present invention, which will become apparent upon examining the following detailed description of embodiments thereof, taken in conjunction with the attached drawings.

BRIEF DESCRIPTION OF THE DRAWINGS

Throughout this document, drawings are provided to illustrate various embodiments of the invention. Reference numbers may be re-used to indicate correspondence between referenced elements. The drawings are provided to illustrate exemplary embodiments described herein and are not intended to limit the scope of the disclosure.

FIG. 6K shows an example in which an amount of rotation of trunk between starting posture and loading phase becomes a number characteristic of the initial preparation, while an amount of knee rotation during swinging phase indicates the level of the kick;

FIG. 8B shows a schematic representation of a recognized motion by SEDA1 and SEDA2, where start and end of motion are visible together with the ball hit event;

FIG. 8C shows each phase can be further described and split into sub-phases by means of an event different from the ball hit event;

DETAILED DESCRIPTION OF THE PREFERRED EMBODIMENTS

The detailed description of the present invention is presented largely in terms of procedures, steps, logic blocks, processing, or other symbolic representations that directly or indirectly resemble the operations of data processing devices. These descriptions and representations are typically used by those skilled in the art to most effectively convey the substance of their work to others skilled in the art. Numerous specific details are set forth in order to provide a thorough understanding of the present invention. However, it will become obvious to those skilled in the art that the present invention may be practiced without these specific details. In other instances, well known methods, procedures, components, and circuitry have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments.

The present invention pertains to a system, a method, a platform and an application each of which is uniquely designed, implemented or configured to use distributed placement of sensor modules for capturing and analyzing motions of a human being performing various activities (e.g., per a sport). In one embodiment, full and/or partial body motion capture and analysis are performed using an application-oriented, multi-sensor, high-speed algorithms and scalable system platform. As used herein, any pronoun references to gender (e.g., he, him, she, her, etc.) are meant to be gender-neutral. Unless otherwise explicitly stated, the use of the pronoun "he", "his" or "him" hereinafter is only for administrative clarity and convenience. Additionally, any use of the singular or to the plural shall also be construed to refer to the plural or to the singular, respectively, as warranted by the context.

To facilitate the description of the present invention, one of two specific sports such as martial arts and tennis are used as an example to illustrate how one embodiment of the present invention is used to detect and analyze motions in a sport. Those skilled in the art shall appreciate that the present invention can be applied to other sports, applications and common platforms. Embodiments of the present invention are discussed herein with reference to FIGS. 1A-8H. However, those skilled in the art will readily appreciate that the detailed description given herein with respect to these figures is for explanatory purposes only as the invention extends beyond these limited embodiments.

Figures 1A, 1B:
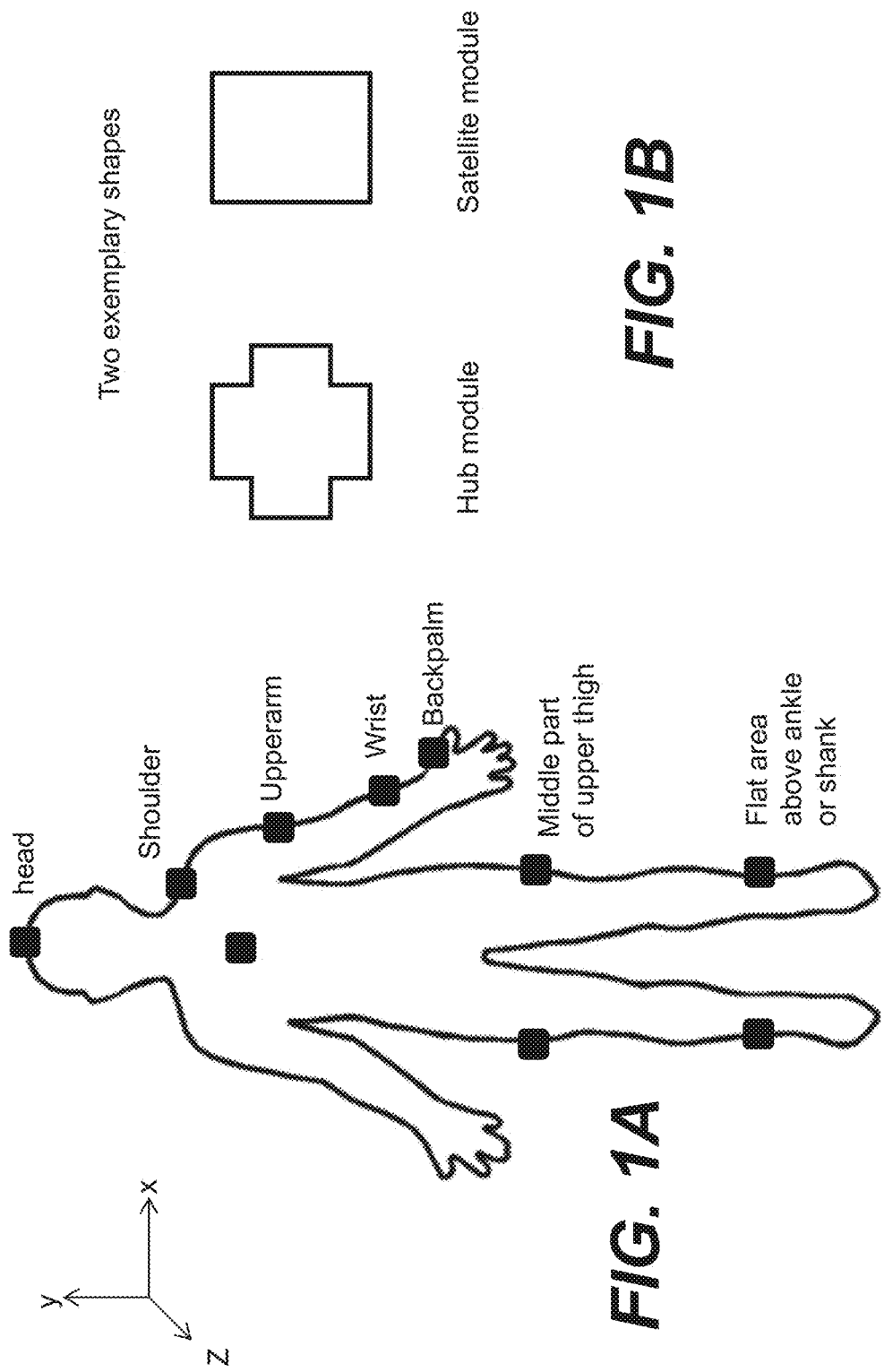
FIG. 1A shows there are a number of sensor devices or modules placed respectively on certain human body parts.
FIG. 1B shows two exemplary types of the modules, a satellite module and a hub module, wherein the hub module is made in a different shape from that of the satellite modules for easy recognition.

Referring now to the drawings, in which like numerals refer to like parts throughout the several views. FIG. 1A shows there are a number of sensor devices or sensor modules placed respectively on certain human body parts. Depending on implementation, each of the sensor modules includes one or more inertial sensors that produce sensing signals when the modules are caused to move around. The sensing signals are sampled periodically (e.g., every 10 millisecond) to produce sensing samples or data.

In one embodiment, a system including one or more computing devices is designed to collect some or all the sensor samples from the sensing modules attached to a user (e.g., a human performing certain activities) and track at every sample point if needed. The system is remotely located with respect to the modules, also referred to as a server, a cloud computer or simply cloud, and configured or designed to perform motion analysis by processing a set of raw sensor samples received remotely from the hub module, and derive joint angle outputs to detect start/end of motion, classify a motion type (e.g., forehand topspin, backhand slice, flat serve, etc.) and compute important attributes of the motion (e.g., injury risk evaluation, footwork quality metrics, power metrics, ball contact height estimate, etc.). The motion capture's body segment frames and motion analysis' attributes are then sent to a designated app (e.g., tennis app) running in a mobile device, for 3D graphics rendering into a human avatar animation and motion chart analysis.

FIG. 1B shows two exemplary types of the modules, a satellite module and a hub module. For ease of identification, the hub module or hub is designed to have a unique shape, different from the rest of the satellite modules. A hub module is made in a distinct "+" medic shape in one embodiment. In some embodiments, the satellite modules connect wirelessly to a single Hub module, for example, via Wi-Fi, Bluetooth, and etc. In one embodiment, the modules may communicate via a proprietary high-speed 2.4 GHz protocol. For tennis, the hub module may be typically placed at the chest location and is configured to combine the sensor data with the same timestamp and streams, for example, via externally Wi-Fi or Wi-Fi-Direct to a cloud datacenter or a mobile device (phone, tablet, or laptop).

According to one embodiment, raw sensor data is at 100 Hz sampling rate and processed by a cloud server or a mobile device for motion capture and motion analysis. Motion capture involves a set of mathematical equations to track each joint angle. The system may perform motion analysis by processing a set of raw sensor samples and joint angle outputs to detect start/end of motion, classify the motion type (e.g., forehand topspin, backhand slice, flat serve, etc.) and compute certain attributes of the motion (e.g., injury risk evaluation, footwork quality metrics, power metrics, ball contact height estimate, etc.). Since the modules are respectively attached to different parts of a body, the sensing data from each of the modules can be used to analyze attributes of the motion made at each of the body parts. In one embodiment, the body segments along with the data frames as well as the motion attributes can be sent to an App (e.g., a tennis application) running on a mobile device, for 3D graphics rendering into a human avatar animation and motion chart analysis.

Figure 2:
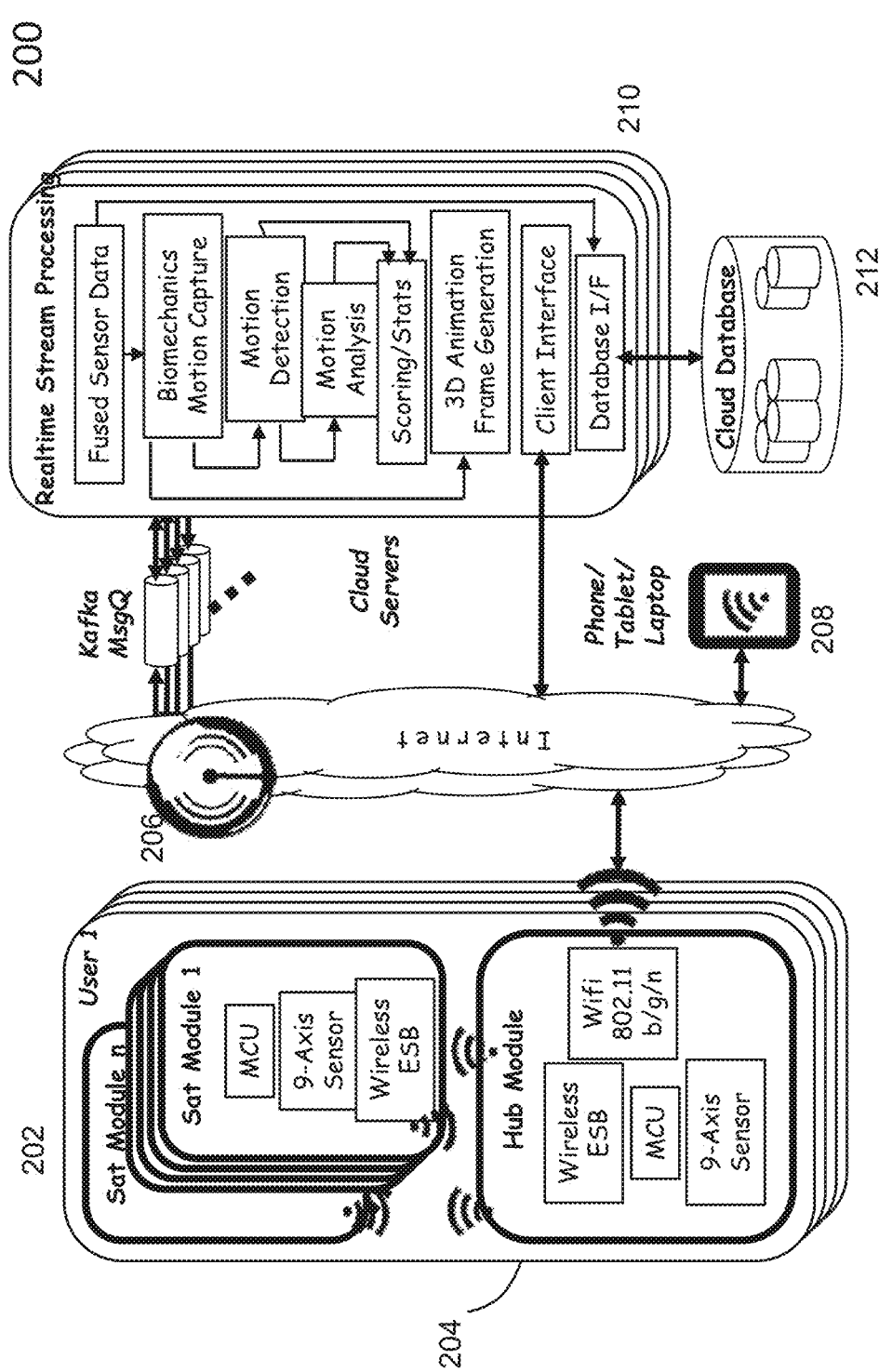
FIG. 2 shows a system configuration according to one embodiment of the present invention.

FIG. 2 shows a functional block diagram 200 according to one embodiment of the present invention. A user is attached with wireless sensor modules 202 that are relatively small in size and light in weight. The number of sensor modules 202 and placement can be determined depending on a target application and types of motion to be captured and analyzed. According to one embodiment, each sensor module comprises:

- a 9-axis sensor chip having integrated 3-axis gyroscope, 3-axis accelerometer, 3-axis magnetometer, such as those manufactured by Invensense;
- a 32-bit ARM Cortex M4F microcontroller (MCU) with floating point arithmetic unit (FPU) to perform floating-point math-intensive sensor fusion processing at every sensor module, such as those manufactured by Freescale; and
- a wireless chip with embedded 32-bit ARM Cortex M0 MCU to support 2 Mbps wireless communication, such as a Nordic 2.4 GHz wireless chip.

In one embodiment, the wireless chip is based on a proprietary and enhanced Shockburst protocol, which has been deployed for medical/industrial devices. Other standard wireless protocols like Bluetooth/BLE, Ant+ and Zig-Bee may also be employed.

One of the sensor modules 202 is designed to function as a hub 204 of all the satellite sensor modules, controlling and collecting sensor data from the satellite sensor modules. The sensor data from the satellite sensor modules are received and combined with the sensor data generated in the hub 204 into one record having the same timestamp and streamed out to the cloud. Typically, the sensor data sampling rate is at 100 Hz, producing gyro x/y/z, accel x/y/z, mag x/y/z, and quaternion w/x/y/z values for each satellite every 10 milliseconds. To get robust data bandwidth and wireless distance to a Wi-Fi router/hotspot, the system may include a Wi-Fi module supporting 802.11b/g/n. In the absence of Wi-Fi router/hotspot, the hub module can stream the sensor data directly to a mobile device 208 (e.g., smartphone/tablet/laptop), for example, via Wi-Fi-Direct protocol. If the mobile device 208 has limited computing resources compared to one or more cloud servers 210, motion capture/analysis may be performed based on reduced information from the sensor modules, but overall still delivering the benefits in the present invention.

In the presence of an Internet connection 206 to a cloud datacenter (e.g., the servers 210), the captured and combined sensor data records are streamed continuously to the cloud datacenter. The data stream queuing and processing may use a framework suitable for real-time stream analytics and having sub-second response time. In one embodiment, the system uses open-source software components, such as Kafka (for message queuing), Jetty (for application session management), and Reserve (for executing R math programs).

With a Kafka framework, the system can queue sensor data streaming from thousands to millions of users, while maintaining low latency requirement for real-time processing. Multiple sensor records may be batched to be processed by the known R math program. One or more R processes may be dedicated for each user to compute the following: Joint angle estimate of each joint based on multi-sensor data and human biomechanics model, rotational direction values of corresponding body segments, detection of the start, middle, end, and type of a motion that is unique to a target application, all based on a sequence of multi-sensor samples (called frames).

For example in tennis, a motion could be a forehand topspin with start frame at ready position, middle frame at ball contact, and end frame at completion of swing follow through. The motion is analyzed for different attributes or statistics, such as (for tennis) number of repetitions, footwork quality metrics (number of steps before ball contact, knee bend angle, balance), power metrics (swing speed, hand acceleration, ball strike zone), injury risk analysis (elbow, shoulder, wrist, back, knee), and etc., all based on the available joint angles, approximate rotation values of all 21 segments of human skeleton (wire body) that is ready to be rendered and animated by a 3D graphics software like Unity.

To complete the streaming, the output of joint angle processing and motion attributes/stats can be streamed out to the user's mobile device to be further processed for live avatar animation and chart view creation. For playback and data analytics, every user's recording session may be stored in a cloud database. Both the raw sensor data input and output results (e.g., joint angle frames, motion attributes/stats) can be part of the session record. For animation playback and chart views, the output data may be retrieved and sent to a mobile device. When there is enhancement or addition to the motion capture and motion analysis algorithms, the system can re-generate the output results from the original input data.

The overall system stack comprises layers of hardware, firmware, wireless network, cloud infrastructure, real-time streaming software, biomechanics motion algorithms, database, big data analytics, 3D graphics, and a user interface. The following table summarizes the various aspects of the system.

| Requirement | System Feature |
|---|---|
| 1. Capture and analyze human motions with or without camera | Employ inertial sensor chips in smartphones and wearables to track movements. Multiple inertial sensors may track movement of body segments. To get better sensor fusion and positioning accuracy, a processor is employed to integrate all 3 micro-electro-mechanical (MEM) accelerometer, gyroscope, and magnetometer. To further improve human motion capture and analysis, biomechanics modeling and knowledge of the target application's activities are combined. |
| 2. Instant biomechanics feedback | System performs high-speed algorithms to analyze motions based on human biomechanics model, joint angles, raw sensor data, and sensor fusion. System incorporates proper biomechanics knowledgebase and patterns into the motion library to compare with, based on the specifics of target application. These algorithms require substantial mathematical computations. To give instant feedback in sub-second, the system provides a real-time stream processing in the cloud for scalable computing. |
| 3. Injury prevention analysis | The system may incorporate injury analysis and motion library patterns/signatures based on studies in biomechanics, physical therapy/rehabilitation, sports medicine, and experiments in the target application area. The system may continuously add more injury patterns into the motion library and algorithms and allow users to add their own injury patterns to recognize possible injury. |
| 4. Live remote motion monitoring or coaching | In one embodiment, the system leverages the cloud capabilities to enable real-time motion monitoring of a user by other authorized users (coach, doctor, supervisor) from any distant places. Unlike video monitoring, the sensor stream bandwidth requirement may be several orders of magnitude less. |
| 5. Share motion recordings with authorized users | In one embodiment, the system leverages the cloud infrastructure to share motion recordings with other authorized users. The system may record both the raw sensor data input and output results (animation frames, motion attributes). When there is enhancement or addition to the motion capture and motion analysis algorithms, the system can re-generate the output results from the original input data. |
| 6. Data analytics insight | The system may store all user profiles and recordings in the cloud's scalable database/storage. The system may deploy big data analytics tools and search queries to gain insight information upon request on user's own data, or anonymous business intelligence. |
| 7. Scalable and adaptable to many target applications | The system platform is based on an architecture with common building blocks that can scale and adapt to customization and many target applications. In one embodiment, the system leverages cloud's "infinite" computing resources to scale increased application complexity, the number of active users, concurrent sessions at peak usage, and newly developed applications. The system may implement on-demand cloud resource management with load balancing to handle changing requirements and demands. |
| 8. Affordable | The system may optimize COGS (cost of goods sold) by choosing commodity/volume hardware components, cost-efficient contract manufacturers, and license-free open source software packages. The system may optimize operational costs through on-demand cloud resources. |
| 9. Easy to use | The system may use an intuitive UI (user interface) with game technology where users of all ages can operate easily without a manual or complex instructions. The system may select features that give most benefits to users and present the feature capabilities in multi-level UI, starting from simple to deep analysis. The system may use sensor packaging and harness designed for simplicity and ease of use. |

Figure 3A:
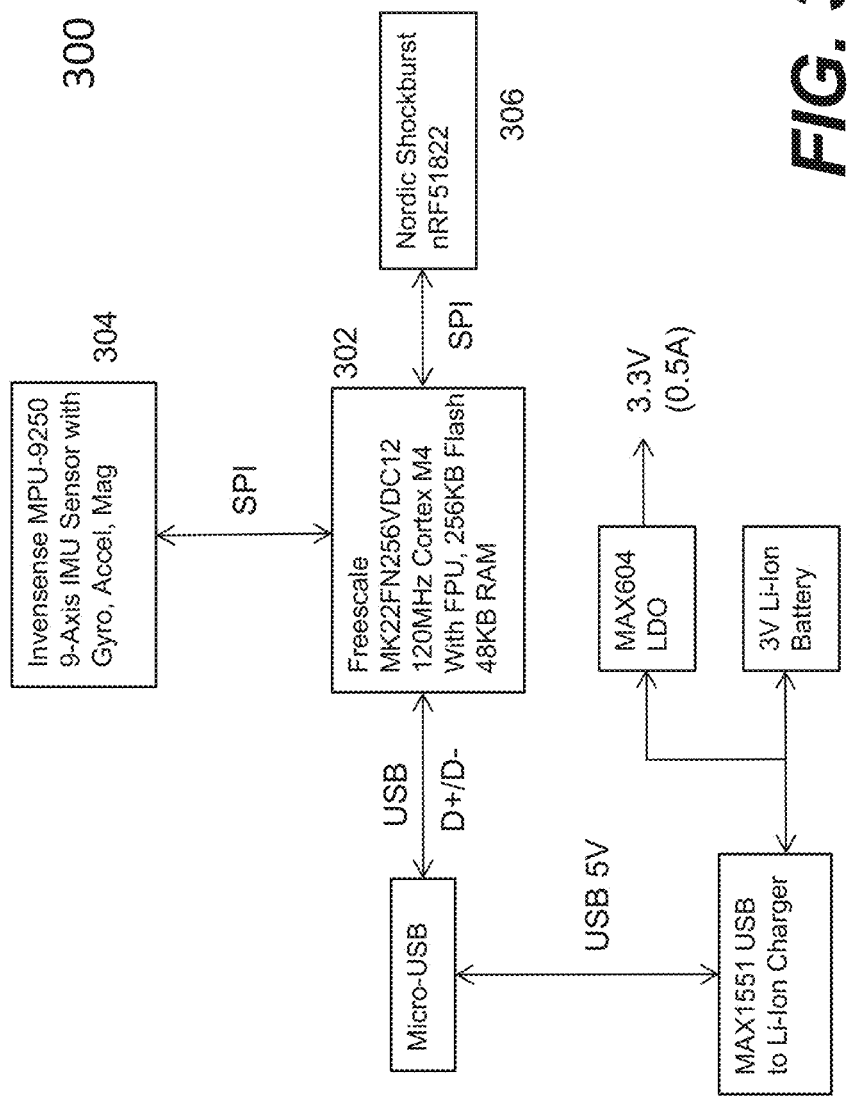
FIG. 3A shows a function block diagram of a satellite module according to one embodiment of the present invention.

Referring now to FIG. 3A, it shows a functional block diagram of a satellite module according to one embodiment of the present invention. There are essentially three primary components: a microcontroller (e.g., Freescale K22F 32-bit ARM Cortex M4F with floating point unit), a transceiver (e.g., Nordic nRF51822 having 32-bit ARM Cortex M0), and motion sensors (e.g., Invensense MPU-92509-axis inertial sensor chip). Other remaining components include a rechargeable battery, a USB battery charger chip, a low-dropout (LDO) voltage regulator, and a micro-USB connector. Besides for charging, the micro-USB connection is also used for firmware upgrade and serial communication.

Figure 3B:
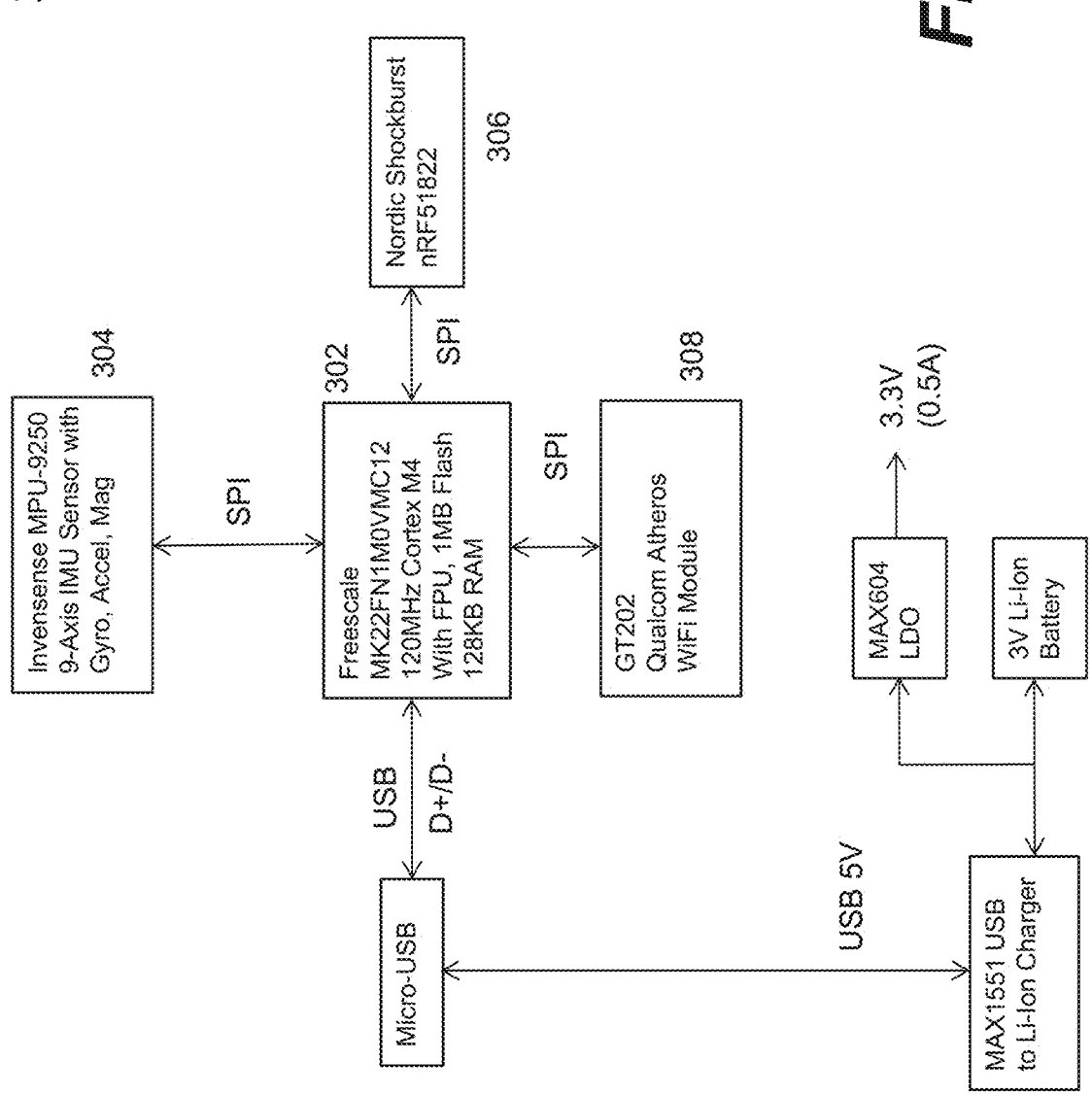
FIG. 3B shows a function block diagram of a hub module according to one embodiment of the present invention.

FIG. 3B shows a functional block diagram of a hub module according to one embodiment of the present invention. In comparison with a satellite module shown in FIG. 3A, a hub module includes an additional component to communicate with the satellite modules to receive the sensor signals therefrom. In one embodiment, the additional component is based on a Wi-Fi module (e.g., QUALCOMM Atheros GT202 Wi-Fi module) to enable the hub to communicate with the cloud directly via Wi-Fi Internet connection, or to a mobile device via Wi-Fi-Direct protocol. It gives the hub a longer range and higher bandwidth wireless capability than the typical Bluetooth/BLE based wearable products. In one embodiment, the microcontroller used is Freescale K22F MCU having 128 MB RAM and 1 MB flash memory.

To make the hub module and its satellite modules operate as a complete wearable system, appropriate firmware (embedded software) is specially designed to tie the different components in each of the modules to operate as a synchronized unit and communicate with the cloud and/or a mobile device having a designated App (e.g., referred to as Turing-Sense App) executed therein. The firmware is designed to manage how the data flow and control flow are performed between or among the hub and satellite modules, a process (e.g., an algorithm) of internal star wireless network among the modules, a wireless frequency hopping method, how to set the satellite device list, compacting sensor data, wireless error correction, and clock skew mitigation.

Figure 4:
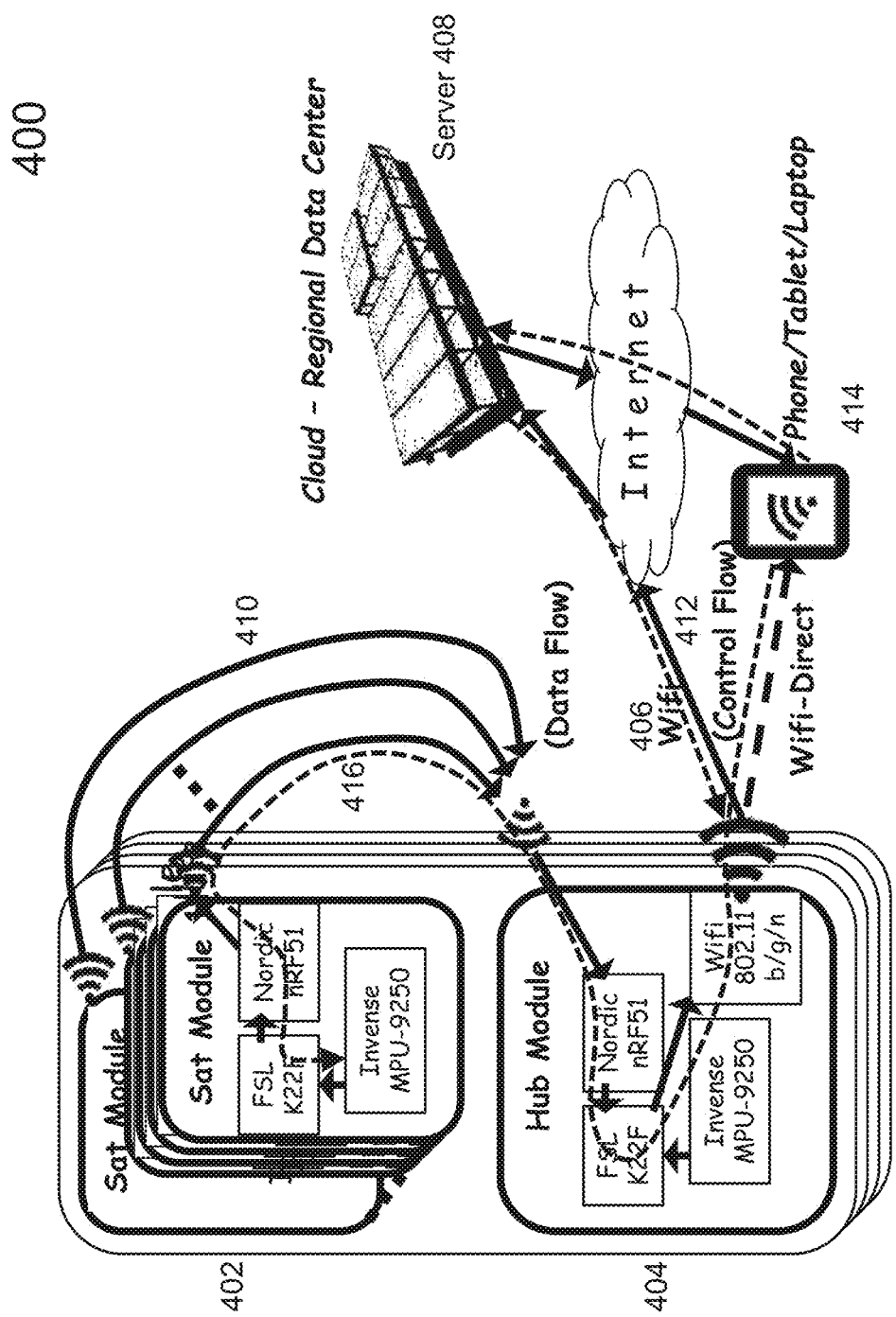
FIG. 4 shows a sensor data flow in arrows from multiple satellite modules to a hub module, where the hub module streams the combined data flows via Wi-Fi Internet connection to a server (e.g., a cloud regional data center)

According to one embodiment, FIG. 4 shows a system block diagram 400 with a sensor data flow in arrows from multiple satellite modules 402 to a hub module 404 that then streams the combined data flows via Wi-Fi Internet connection 406 to a server 408 (e.g., a cloud data center). It is assumed that the modules 402 and 404 are respectively placed on designated parts on a user. FIG. 1A shows some of the exemplary body parts of a user. As the user makes different moves (e.g., per a sport), the sensors in the each of the modules 402 and 404 generate corresponding sensor data. The sensor data 410 from the satellite modules 402 are transmitted to the hub module 404 that combines the respective sensor data including those generated within the hub module 404 and transports the data 412 to the server 408. The combined raw sensor data as a record is then processed in the cloud 408 for motion capture and motion detection/analysis, where the body frame and biomechanics attributes are sent to a designated mobile device 414 (e.g., a mobile device associated with the user) for real-time 3D animation and motion analysis chart views. In one embodiment with the absence of Wi-Fi internet connection, the hub module 404 streams the sensor data to the mobile device 414 via Wi-Fi-Direct protocol, and all the motion capture and analysis are processed and displayed in the device locally. Later when the device 414 is connected to the Internet, the recorded data is uploaded to the cloud.

During these data flows, if one of the satellite modules 402 is not ready to send out its data stream, the hub module 404 detects which one of the satellite modules 402 and sends a control flow command (shown in a reverse arrow 416 of the data flow) to backpressure the satellite module. This is an important mechanism so that while the system can stream as fast as it could, it is adaptive to self-throttle at the same time.

The following describes an internal star wireless network process based on an algorithm using an Enhanced Shockburst (ESB) high-speed (2 Mbps) protocol. ESB is a proprietary wireless protocol with packet header and payload definition of a simple/barebone physical media network layer. It does not have the overhead and baggage like Bluetooth/BLE, ANT+, ZigBee, and other standard wireless protocol. Built on top of the ESB layer, a proprietary "star" network protocol is designed to connect many satellites to a single hub. According to one embodiment, the pseudocode of firmware is assumed to be running on the Nordic 32-bit ARM Cortex M0 microcontroller in the satellite modules and hub Module.

The following pseudo code provides an example of the satellite's main loop in Nordic:

```
loop forever {
    print to logs
    if a hub control packet came in (and CRC is good) {
        obey any commands to set the RTC or change state
        if the packet is asking you to speak,
            if its echoed CRC matches last data packet sent,
                fill a new data packet from the cbuf and send it
            else
                re-send the data packet you already built
        if you sent rows {
            try to get that many rows from SPI
        }
    }
    if it's been long enough, & you aren't desperately trying
    to drain the queue {
        read a row from SPI
    }
}
```

The following pseudo code is used for the hub's main loop in Nordic:

```
loop forever {
    if should set timestamp {
        start internal RTC
        note the timestamp to set
    }
    choose next satellite which should speak
    build control packet:
        should the satellites be sensing? sending?
        do the satellites' RTCs need to be set?
        include the CRC of the last packet you received from this satellite
    send the packet, wait for a reply (with a non-corrupt timestamp) from the
    satellite
    if one comes in,
        remember it
        if the timestamp has advanced from that satellite's last packet,
        the old packet is real. push its rows into the cbuf
    print to logs
}
``` and then on SPI callback it builds the next packet . . . filling it with rows from the cbuf if there are any and if the freescale has sending turned on.

According to another embodiment, wireless frequency hopping may be used so that satellite modules find the hub and the hub finds the satellite modules, where a channel is chosen for the group that is free of interference. In the frequency-hopping scenario, the hub will establish a communication session with the satellite modules in a free "channel" pair. However, if during communication, the hub experiences a downgrading performance with a satellite module, it will try to find another set of "channel" to speak to the satellite module.

In one embodiment, the Nordic chip supports frequencies from 2.400 GHz to 2.526 GHz. These are described as "channels" 0-126, with each channel having a 1 MHz band. For full speed ShockBurst, the system may double this bandwidth. In other words, using ESB channels that are at least two apart to prevent interference.

In another embodiment, the firmware is designed to assume that a particular ESB channel is always used as a designated channel (e.g., an StM "Slave-to-Master" or MtS "Master-to-Slave" channel). Further, the system may be configured such that StM channels and MtS channels are specified in pairs, in other words, there is a pair of inbound and outbound channels. That is, if the MtS channel is ESB channel "2", the StM channel would then be channel "5" to skip channels "3" and "4", a 3 MHz band instead of 2 MHz. Thus, for StM channel "2", the system may occupy channel "2" and "3", "4", and its corresponding MtS channel "5", and "6" "7", for a total of 6 channels.

This leaves a set of 21 LCP (Logical Channel Pairs). In the USA, only the frequency range of 2,400-2,483.5 MHz is permitted for unlicensed use. In other words, channels 0-83 are only used, which means there are 14 logical channel pairs. It is these LCPs that are referred to as "channels" for some embodiments deployed in the USA. Thus, a channel represents the pair of adjacent channels—the MtS and StM together. Both are included in this check, because the round trip goes through both channels, and it is successful round trips that the hub is measuring.

In one embodiment, on a given channel, the hub module talks to all of its satellite modules (or tries to), respectively. After a predefined number of trips (e.g., four trips) through the satellite list, if the number of successful round trips is ⇐60%, the hub moves onto the next channel. This may occur even if the hub has settled on a channel. The hub monitors the last four trips through a satellite list so it can notice any degradation in communication. When the hub moves on to a new channel, it first sends out a special control packet warning the satellite modules of the fact. The satellite modules follow anyway because their hub is vanished from the original channel. Further, this may be used as a precaution because the satellite modules following immediately makes it easier to get a good measurement of the QoS on the new channel.

On any given channel, when unpaired, a satellite module is caused to listen for a predefined time (e.g., 16 ms) to see if a hub is there in a channel. If not, it moves on. If so, it listens through the hub's entire round-robin loop, to see if its own name will be called. If so, great; here's where it will stay until it doesn't hear the hub for 26 ms, or its own name for 3 go-arounds. If its own name isn't called, it moves on.

In one embodiment, the satellite modules are designed to have assumptions that during communication with a hub, the hub may actually change from one hub to another hub. It may be slow for a satellite module to find its hub. For example, if a user is at a Tae Kwon Do studio or some place with a large number of hubs (carried by other users). To get around this, a method referred to as imprinting may be used. In one embodiment, imprinting means that a satellite module is programmed or hard-coded, hence imprinted, to communicate with a particular or designated hub. Instead of waiting for a predefined time (e.g., 16 ms) on a channel to see if a hub is there, a satellite module is designed to wait for a particular hub, that is the last hub that called the name (e.g., identifier) of the satellite module and shun others. That imprinting can be broken if a satellite module goes for a few cycles without seeing that hub, or if a predefined time is gone near a hub but the hub did not call the identifier of the satellite module anymore.

In one embodiment, the hub module may call itself Device 0, and always assumes that the satellite modules are Devices 1, 2, . . . N. In another embodiment, each device may have a 32-bit serial number as an identifier, and the hub module talks to the satellite modules that the cloud specifies.

Instead of going round-robin from 1 to N, the hub module may go round-robin along the list of satellite modules given by the command. In addition, in some cases, the system may make a change to the length of the satellite modules list, and in some cases change to a maximum number of satellite modules that the hub will need to support a predefined number of satellites (e.g., 14 satellite modules).

For frequency hopping, the hubs may be distinguishable from each other (i.e., have different device IDs). The hubs may also be distinguishable from satellites. For example, the high byte of hub serial numbers may be set to something different than that of satellites. In one embodiment, the system (hub and satellite) sends the quaternion data as four floats (32 bits each). Floats may accommodate any value from 0 to infinity. If the quaternions are represented as enums and bounded fields (0-N), the system may save storage space without losing any important data. In one embodiment, quaternions are a vector with a direction (orientation axis of the sensor) and a magnitude (rotation around the axis). The magnitude may be stored separately, and then, the x, y, z of the vector can be scaled up and down freely. In other words, a quaternion {w, x, y, z}={120°, 1, −2, 3} is completely equivalent to {120°, ⅓, −⅔, 1}. In fact, any quaternion can be written with the biggest of its x/y/z values=1 or =−1, in which case the other two terms will always be scaled down to between −1 and 1 inclusive.

The following data structure is one example that may be used in the embodiments:

```
typedef enum {
    INVALID, /* for an all-zero quaternion */
    X_POSITIVE_1,
    Y_POSITIVE_1,
    Z_POSITIVE_1,
    X_NEGATIVE_1,
    Y_NEGATIVE_1,
    Z_NEGATIVE_1
} unit_vector_component_t;
struct {
    unit_vector_component_t unit_component;
    int16_t first_term /* -32767 = -1.0, 32767 = 1.0 */;
    int16_t last_term /* -32767 = -1.0, 32767 = 1.0 */;
    uint16_t w; /* 0 = 0°, 65536 = 360° */
} vector_t;
```

As shown in the example above, {120°, 1, −2, 3} would be encoded as {unit_component, first_term, last_term, w}={Z_POSITIVE_1, 10922, −21845, 21845} 3 is the most significant, so instead of being stored literally, unit_component states that it is the one equal to 1, hence Z_POSITIVE_1. Thus, in a normalization process x=1, which becomes x=⅓, which becomes 10922 (⅓ of max_int32). When y=−2, which becomes y=−⅔, which becomes −21845 (−⅔ of max_int32). When there is an angle of 120 degrees, it becomes 21845 (⅓ of max_uint32).

Below is exemplary pseudocode:

```
encode(w, x, y, z):
    output.w = w *65536
    if x, y, z are all 0:
        output.unit_component = INVALID
    else if greatest of abs(x), abs(y), abs(z) is x:
        output.unit_component =
            X_POSITIVE_1 if x>0 else X_NEGATIVE_1
    first_term = (y/x)*32767
    second_term = (z/x)*32767
        else if it's y:
            output.unit_component =
                Y_POSITIVE_1 if y>0 else Y_NEGATIVE_1
    first_term = (x/y)*32767
    second_term = (z/y)*32767
        else if it's z:
            output.unit_component =
                Z_POSITIVE_1 if z>0 else Z_NEGATIVE_1
    first_term = (x/z)*32767
    second_term = (y/z)*32767
    return output
decode(unit_component, first_term, second_term, w):
output.w = w / 65536
if INVALID:
    output.x = 0, output.y = 0, output.z = 0
    else if X_POSITIVE_1 or X_NEGATIVE_1:
output.x = 1
output.y = first_term / 32767
```

```
            output.z = second_term / 32767
        else if Y_POSITIVE_1 or Y_NEGATIVE_1:
            output.x = first_term / 32767
            output.y = 1
            output.z = second_term / 32767
        else if Z_POSITIVE_1 or Z_NEGATIVE_1:
            output.x = first_term / 32767
            output.y = second_term / 32767
            output.z = 1
        if unit_component is a _NEGATIVE_1:
            output.x = -output.x
            output.y = -output.y
            output.z = -output.z
        return output
```

The following data structure is an example that may be used in one of the embodiments: the above data structure takes up about 6½ bytes. If merged half-byte with the ts_diff in the current RF packets, it reduces the bytes sent per sensor record to 19 or 20 bytes. Encoding may be done in the cloud for storage and to save bandwidth when the data is being sent back to a mobile device, for example, for rendering animated 3D motion playback.

When there is significant corruption of packets between a satellite and a hub, the most common pattern could be localized damage, either at the end of the packet or at the beginning of the packet. The beginning of the packet is hard to solve because it also corrupts the ESB header, and the packet can be difficult to recognize. However, at the end of the packet, it just ends up ruining the last N records. If there is room in the packet after the last record, the system can put one more "row" in a fashion similar to a Golay code for the last record. Golay codes are an error correction code that is of the same length as the original data and can correct up to 12.5% corruption.

Exemplary Clock Skew Mitigation

In one embodiment, the satellite modules are kept in sync, at least in the data. Skew may exist due to initial propagation delay, but the skew can be kept from changing once it exists and prevent the timestamps in the data (as it appears on the hub) from getting further apart from each other. As shown in FIG. 3A, a module K22F is talking to another module Nordic over an SPI (Serial Protocol Interface), entirely or separately from any sensor records it might send, it also includes its current timestamp. The first time it does this, it compares the two numbers, and remembers the original skew. For instance, if the K22F says "My clock reads T+2 ms" and the Nordic's own clock at the moment it receives says "T+3 ms", it assumes there's a 1 ms difference, and that 1 ms difference is normal. But if the difference ever changes, it then assumes that the clock on the K22F is ticking slightly faster or slower than the clock on the Nordic. Thus future timestamps are adjusted accordingly. The Nordic in a hub does the same thing that K22F in a satellite does.

For example, every time it sends out a control packet, it includes a field that indicates "when it is sending this packet out, and its clock says it's T+Xms." Thus, the satellite Nordic now also knows if the hub Nordic's clock is going faster or slower than its own, and if so, by how much. Accordingly, the system can cleanly join those timestamps with each other. If they started out of alignment, they'll stay out of alignment. But if they started in alignment, they'll stay in alignment. Drift over time can thus be eliminated in some of the embodiments. Other ways of dealing with clock skew may also be incorporated in the embodiments.

Cloud Software Design

In one embodiment, the system operates high throughput and low latency, reliable and scalable cloud services in order to achieve the following goals:
- low latency frame data transfer from devices (modules) to the cloud application tier nodes (App),
- virtually no downtime by distributing load to multiple servers via load balancing service (LB),
- quick and reliable messaging services to decouple frame data transfer from the frame processing (Queue),
- streaming frame data processing in the execution engine tier (Exec) using algorithms implemented in R engine (R),
- near real time delivery of calculated angle and motion results from the cloud application tier (App) to clients (Client), and
- persistent, scalable data services for offline data transfer from data store (DB) to caching tier (Cache) to the application tier (App).

Figure 5A:
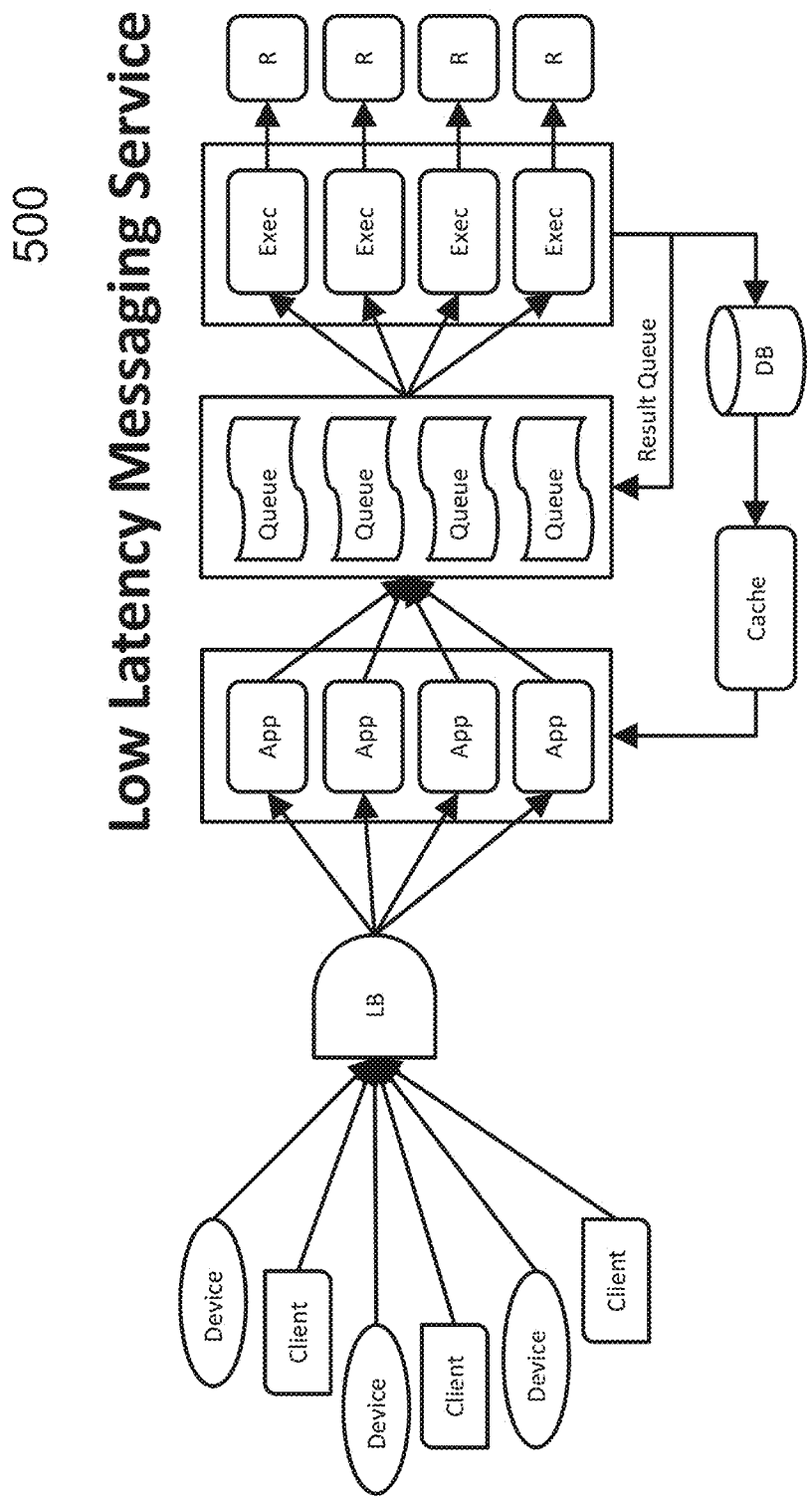
FIG. 5A shows a functional block diagram of the cloud frontend services according to one embodiment of the present invention.

FIG. 5A shows a functional block diagram 500 of the cloud frontend services. In some embodiments, "near real-time" may be based on frames that take 300 milliseconds to 600 milliseconds for the time that covers. For frame data that is generated in a module and ready to transfer to the cloud, the web service requests are sent to the cloud and the device getting confirmation that data has been received. The received data is processed in the cloud, all frame results are calculated, and a client (e.g., a mobile device) retrieves frame results from the cloud and data is ready for visualization.

The data flow may be a stream of raw data frames. In another embodiment, a data frame may be a vector structure representing a collection of metrics collected from a set of sensor modules in a single pass that occurs at a predefined frequency (for example 100 Hz, i.e. a raw data frame is generated every 10 milliseconds).

In a web service implementation, raw frame data are shipped in sets that are defined as: FrameSet=(Fi, Fi+1, . . . , Fj), where i is an index of the earliest raw data frame ready to be shipped, j is an index of the last generated raw data frame ready to be shipped, j>=i, i.e., each frame set contains at least one frame, Time(Fi)<Time(Fi+1)<Time (Fj), namely all frames in a data set are generated in order.

Each frame may belong to a frame set, i.e., a device will ship collected sensor data until the recording stops. Frame data set is encoded and sent as a part of a web service request to the cloud application tier (App). The application tier will pass the message to the data queue in the messaging tier (Queue) and return an acknowledgement that the cloud has received the frame data set and that the device can send the next frame data set.

The messaging tier (Queue) may provide the following functions: Producer/consumer asynchronous access to frame data; message durability for a predefined period of time ensuring that there is no data loss; separation of processing on the application tier (App) and the execution tier (Exec). This means that these two tiers will not block each other during the processing. Each message in the data queue may represent a single frame data set.

The execution tier processes an incoming frame data stream in the same order the frames are generated. While processing the stream, the execution tier (Exec) is designed to recognize the motion, which is defined as a subset of consecutive frames that belong to a specific activity. Motion=(Fi, Fi+1, . . . , Fj), where: i is an index of the first data frame that belongs to the activity, j is an index of the last data frame that belongs to the activity, j>=i, i.e., each motion contains at least one data frame. Not all frames belong to a motion and such frames are considered "inactive". Results of the frame and motion processing are stored in the result queue. These results are provided to the application tier (App) for result delivery to the client application (Client). The client may then send web service requests for all available data in the result queue.

FrameResultSet=(Fi, Fi+1, . . . , Fj), where: i is an index of the earliest data frame that has not been retrieved by the client, j is an index of the last data frame that is available in the frame result queue, j>=i, i.e., each frame result contains at least one data frame. MotionResultSet=(Mi, Mi+1, . . . , Mj), where i is an index of the earliest motion result that has not been retrieved by the client, j is an index of the last motion result that is available in the motion result queue, j>=i, i.e., each motion result set contains at least one motion result, and M is defined as a vector containing a set of elements describing motion statistics.

In one embodiment, application, messaging and execution tiers are implemented in a horizontally scalable manner. They include multiple servers for each tier. All servers implement the same functionality in order to provide transparent failover in case of a single server failure or other network or infrastructure problem that could cause some of servers to be inaccessible.

Figure 5B:
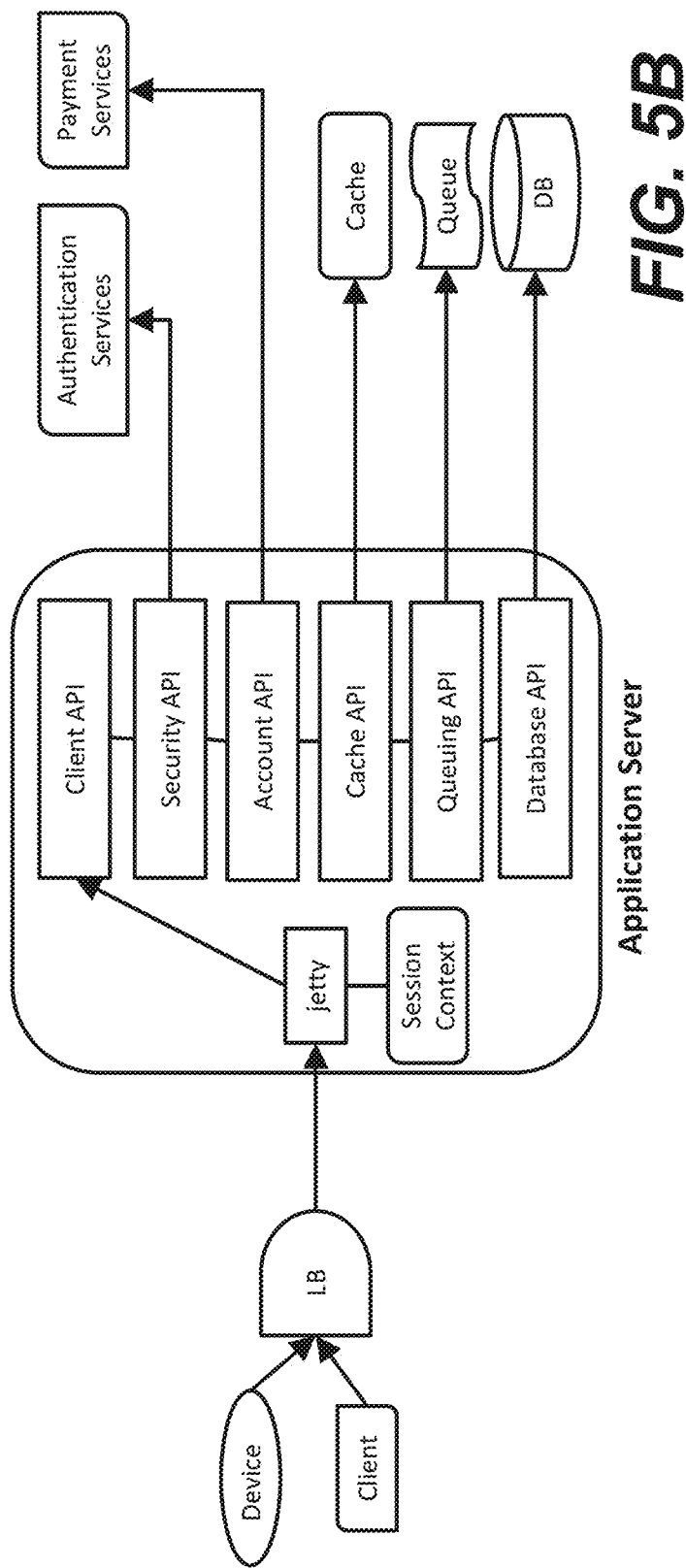
FIG. 5B shows the functional block diagram of cloud client services according to one embodiment of the present invention.

FIG. 5B shows the functional block diagram 520 of cloud client services. The client services share a common set of APIs, where the APIs are a set of exposed web services, available to the sensor modules and client applications. Some of APIs include:

Security API—a private API to implement authentication and authorization services, where the authentication services include external services, such as, via Oauth2 standard;

Account API—a private API to manage all application objects and metadata in the persistent data store. This layer also provides access to external payment services to support license and subscription services;

Queueing API—a private API to store and access frame and motion data required to support real-time services. It may be used to decouple device and client requests from the data processing in the execution layer. This layer is a producer for the Cache API;

Cache API—a private API to implement data caching required to reduce number of physical IO requests for frame and motion data. This layer is a consumer of Queueing API and Database API; and Database API—a private API to allow access to frame and motion data in the persistent data store. This API is a producer for the Cache API.

All transient device and client session properties are stored in the Session Context within the application execution engine (jetty).

Figure 5C:
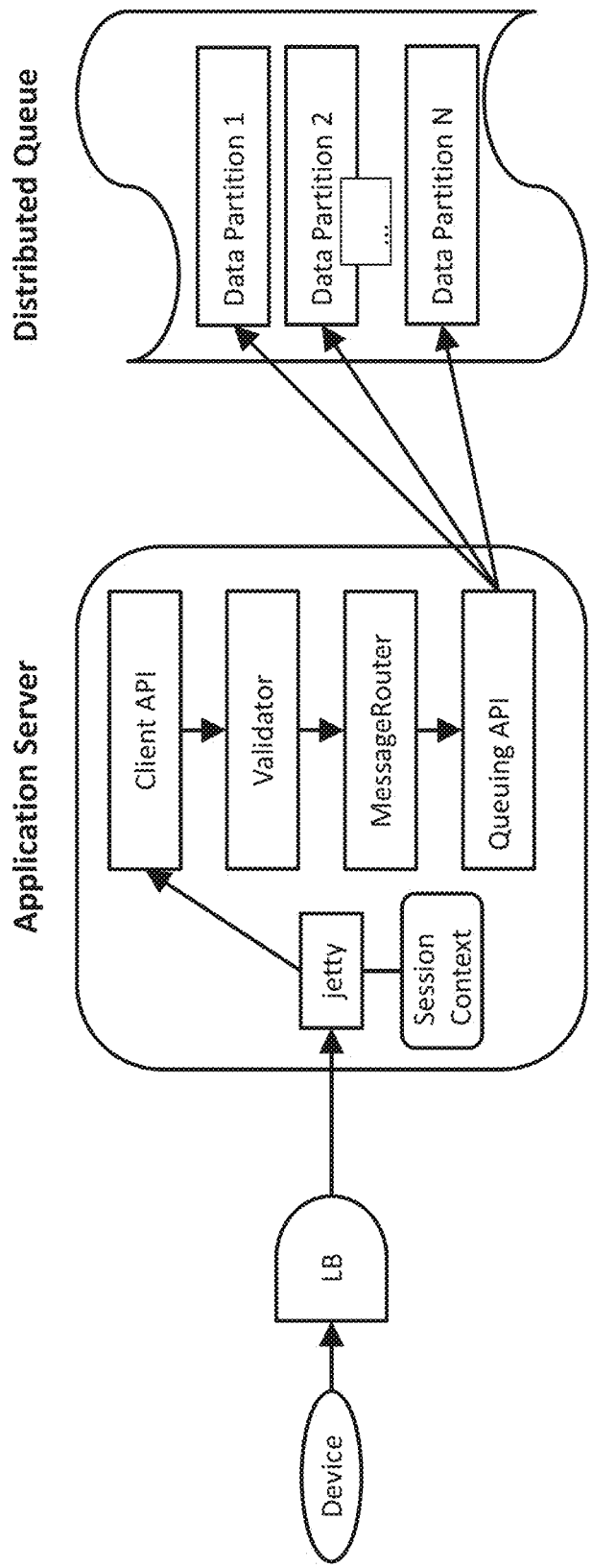
FIG. 5C shows a functional diagram of cloud device data transfer according to one embodiment of the present invention.

FIG. 5C shows a functional diagram 530 of cloud device data transfer. The sensor modules send data to the cloud using Device Data Transfer Web Service. This web service is implemented in the application tier. This diagram 530 describes the data flow on a single application server, but the application tier (App) is implemented using multiple application servers that contain the same code and logic. According to one embodiment:

step 1: Device will execute REST call that includes frame data set with one or more data frames;

step 2: Load balancer will assign the request to a specific application server;

step 3: Jetty service will accept the request and invoke the Client API;

step 4: Client API will decode the message and pass it to the validator;

step 5: Validator checks if the message is coming from the registered (genuine) device;

step 6: MessageRouter implements the algorithm to decide which queue partition will accept the message; and step 7: Queueing API waits for the confirmation from messaging service (Queue).

Result: If the above-described list of steps is completed successfully, send "OK" as acknowledgment to the device. In case of errors where Client API, Validator, MessageRouter or Queueing API fails for any reason, send "ERROR", optionally with the additional error message.

Retransmission: a module is caused to send the frame data set again in case of a failure or timeout. If the number of retransmission requests exceeds the predefined limit, the module will stop data transfer.

Backlog: In case of a high latency and low bandwidth network connection between the hub and the cloud, the number of raw data frames that are not yet sent to the cloud will start to increase, potentially causing device to exhaust available memory space. In such case, the server can be configured to recognize such condition and send the hint as a part of an "OK" message to the device containing recommended frequency at which to send data. This is needed to optimize the network utilization. For example, a cloud service can send back the hint to reduce frame generation rate from 100 Hz to 50 Hz.

Figure 5D:
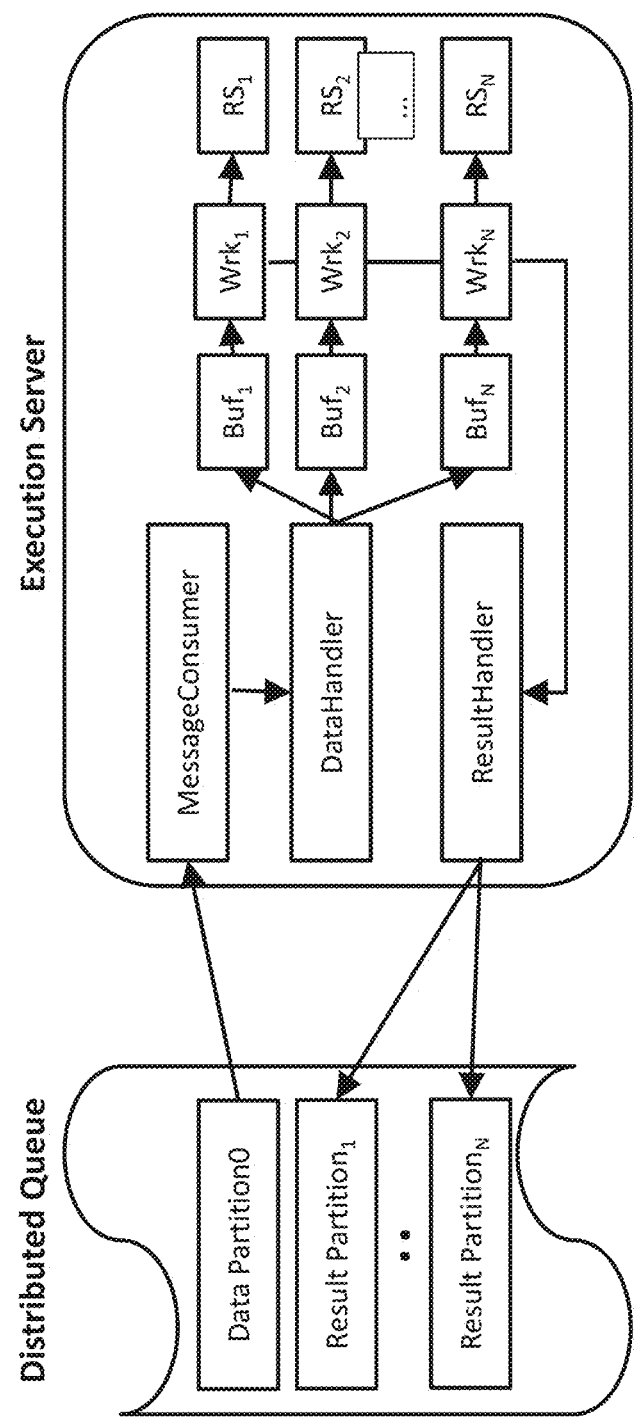
FIG. 5D shows a functional block diagram of frame processing engine which may also be referred to as cloud event processing according to one embodiment of the present invention.

FIG. 5D shows a functional block diagram 540 of frame processing engine 540 which may also be referred to as cloud event processing. An Execution tier (Exec) is implemented using multiple execution servers in the cloud. These servers operate on raw frame data stored in a single data partition in the messaging tier (Queue). The distributed queue is implemented with the low latency, i.e., time between the producer event storing the message in the queue and the time when the same message is available to the consumer allow implementation of near real-time frame processing.

MessageConsumer is running on an execution server and provides the message containing frame data set to the data handler that decides how to route the message to one of the available worker threads (Wrk1, . . . , WrkN). Each worker has its own message buffer (Buf1, . . . , BufN). This buffer allows asynchronous storing of messages by the DataHandler and processing of the message by the worker; they are not blocking each other.

Each worker (Wrk) is connected to the instance of R server (RS) at the moment of worker initialization. This means that connection to R server is always open and data can be efficiently processed removing the overhead of connection handling. The processing of the message in the worker may be implemented using the following algorithm:

step 1: Convert the message containing frame data set to internal data structures in host programming language;

step 2: Pass internal data structures to R server;

step 3: Invoke R server function to process the frame data set;

step 4: Collect the frame result set from R server function calculation; and step 5: Pass the frame result set to ResultHandler.

ResultHandler taked the frame result set and perform the following steps:

step 1: Convert the frame result set to message format required for the Queue;

step 2: Invoke algorithm to decide which Result Partition will accept the result message; and step 3: Store the result message in target Result Partition.

Figure 5E:
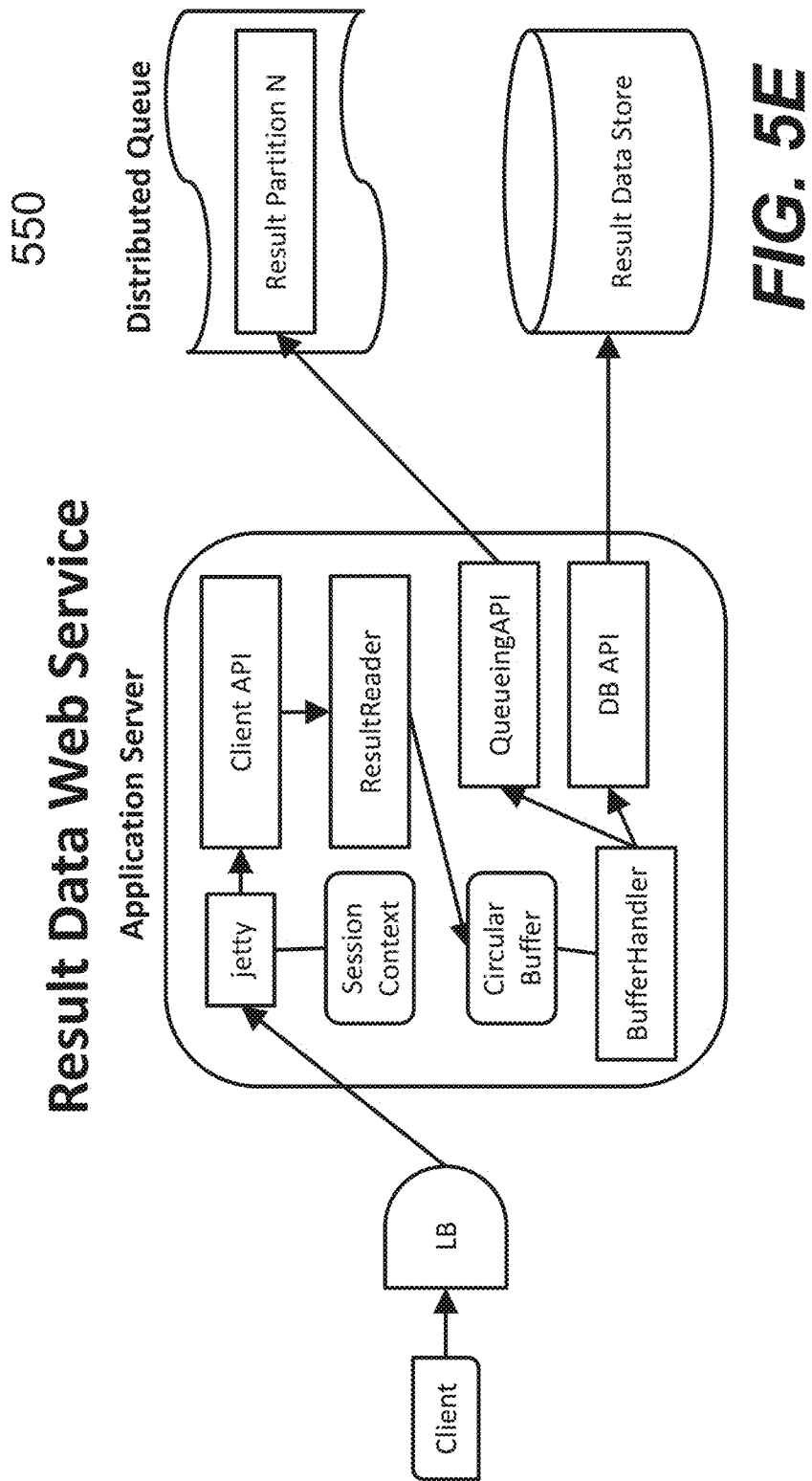
FIG. 5E shows a functional diagram of cloud result data delivery according to one embodiment of the present invention.

In one embodiment, the Execution server avoids the use of file system for interim data. This allows that all data are available in the system memory and processing in a single worker thread can keep up with the rate of data generation by the sense modules. FIG. 5E shows a functional diagram 550 of the cloud result data delivery. A client application sends a request to the cloud Result Data Web Service to get the frame and motion results required for the application functions such as visualization and data analysis. This web service is implemented in the application tier. This diagram describes the data flow on a single application server, but application tier (App) is implemented using multiple application servers that contain the same code and logic. The BufferHandler implements access to Queueing API to fetch data from the Result Partition in case of real-time data processing. In case when the Client requests data that are not real-time, then it uses DB API to fetch stored result data from the persistent Result Data Store. Data are stored in the Circular Buffer and available for the ResultReader in a non-blocking fashion.

step 1: Client will execute REST call that requests result data; request specifies (a) timeout (T) how long application server will wait for result data, and (b) maximum number of frames (N) in the result data set;

step 2: Load balancer will assign the request to a specific application server;

step 3: Jetty service will accept the request and invoke the Client API;

step 4: Client API will decode the request and pass it to the ResultReader;

step 5: ResultReader will wait up to timeout T if there are no data available in the Circular Buffer;

step 6: ResultReader will read up to N frames from the Circular Buffer; and step 7: Client API will assemble the result message and send the response back to the Client.

Result: If the above-described list of steps completed successfully, send response with the result frame set to the client. In case of errors where Client API, ResultReader or BufferHandler fails for any reason, send "ERROR", optionally with the additional error message. Timeouts and errors: the client will try to request the result data set again in case of a failure or timeout. If the number of errors exceeds a predefined limit, the client can stop requesting the result data.

Martial Arts Exemplary Embodiment

To facilitate the understanding of the present invention, the description for a martial arts application is provided herein. In one embodiment, the system is configured to extract movement features from data obtained by in vivo measurement of human body motion tasks using the inertial-sensors technology, creating standard ensemble of knowledge around specific motions and use the above information around specific motions to automatically recognize the type of movement coming from data collected, investigate on its peculiarities, automatically determine the part beyond standard execution of the gestures.

In one embodiment, the system operates according to the following workflow. A set of inertial sensors is positioned on different parts of a user according to a predefined set of rules. A mobile device may be used as a locator machine to examine the sensors outputs in order to verify if the set of rules are correctly followed. Before task execution, the user is asked to carry out a set of predefined tasks or assume specific postures in order to calibrate the system or the set of sensor modules. Multiple calibrations may be performed if needed. Each calibration performed allows the system to calculate constant relations (K) between sensor modules positioned on the body and the body segments upon which they are attached. Each constant relation is calculated so that each body segment can be a reliable representation of anatomy and functionality behind. For each instant of time while a specific task is executed, joint kinematics is calculated in terms of angles of rotation in a 3D coordinate system. Together with the above, inertial quantities for each body segment are obtained from digital manipulation of the outputs from the inertial sensors in the modules. The inertial sensors outputs are then correlated with each other in order to identify specific motion patterns representing a cyclic order of execution of consecutive repetition of the same movement. 3D Joint angles of rotations are correlated with outputs of the inertial sensors so that a phase of movement can be identified. Specific parameters may be generated by comparing the above correlations with a predefined dataset. These parameters may be compared with a dataset coming from a reference database of tasks, obtaining as result how much and in which phase the subject is executing the task differently from the reference.

Figure 6A:
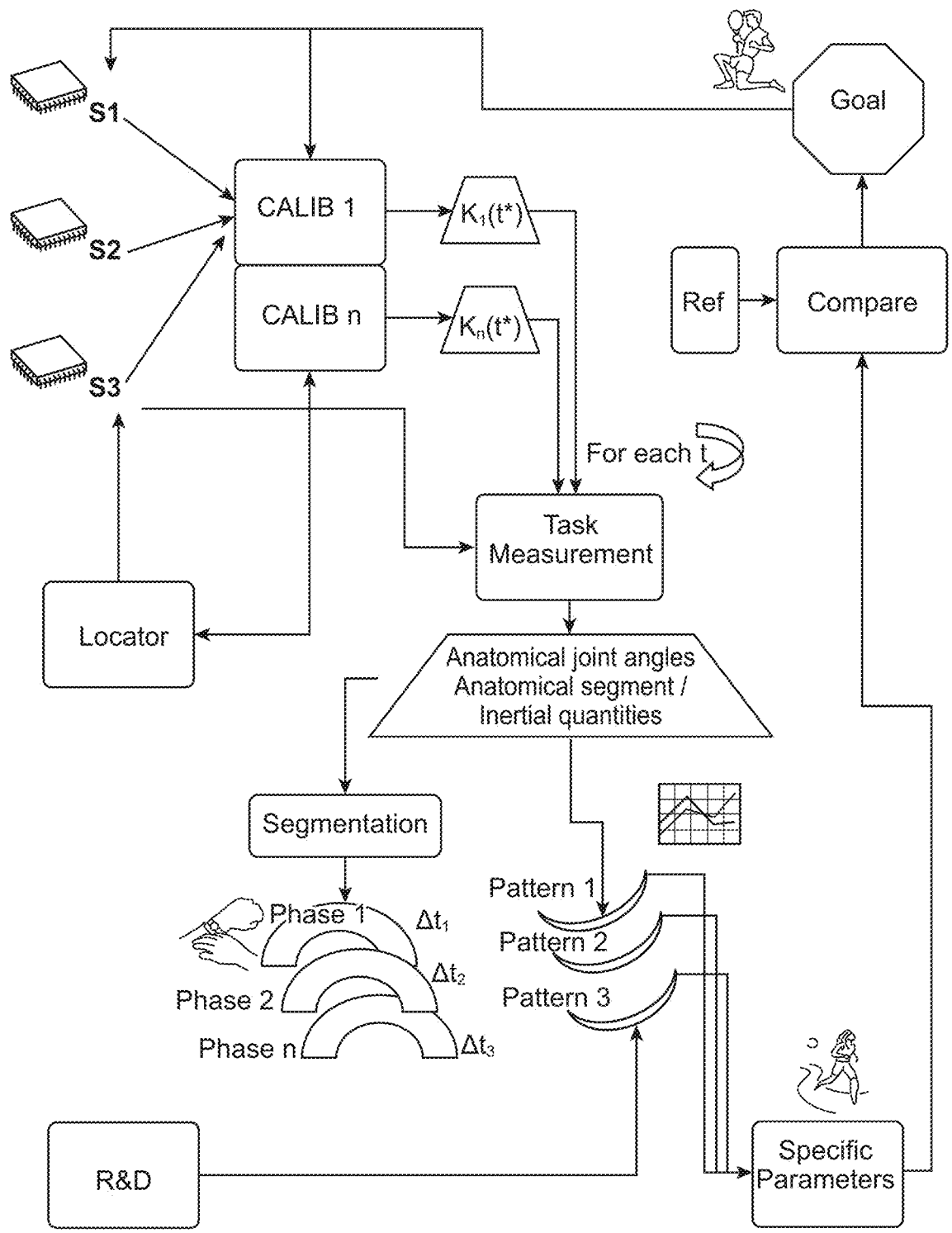
FIG. 6A shows an exemplary system for martial arts.

FIG. 6A shows an exemplary system 600 for martial arts. An inertial-based system is used in order to capture the motion made by a subject or user. The system is made of a specific number of probes, each providing 3D inertial sensors data (acceleration, angular velocity, and magnetic field vector) and 3D orientation data within a common 3D global coordinate system created using the same sensors data at the first frame of analysis. In this text, the sensors data may refer to a single sensor component output or combined sensing data from a sensor module. All sensors are synchronized together in time so that they share the same timing of movement.

Anatomical Description Construction

Figure 6B:
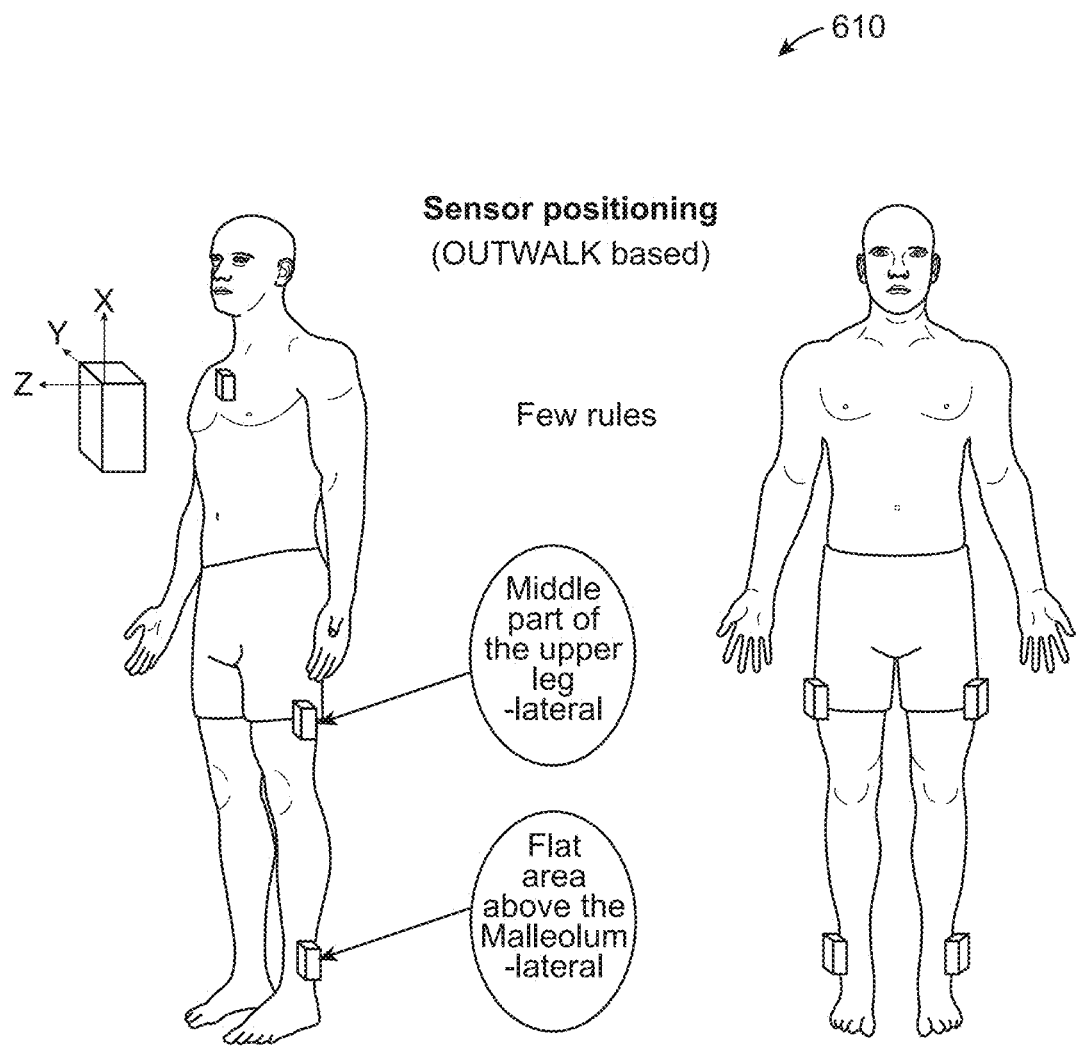
FIG. 6B shows exemplary attachments of the sensor modules for martial arts.

FIG. 6B shows exemplary attachments of the sensor modules 610. Anatomical description of each joint and segment is required in order to quantify all of the segments and joints that are involved in a specific gesture or sequence of gesture. In one embodiment, anatomical description does not simply relay on data coming from the probes and expressed with respect to the global coordinate system. A predefined relation between the probes outside of the body and segments and joints sensed by the system may be used to make the anatomical description.

Calibration

Figures 6C, 6E:
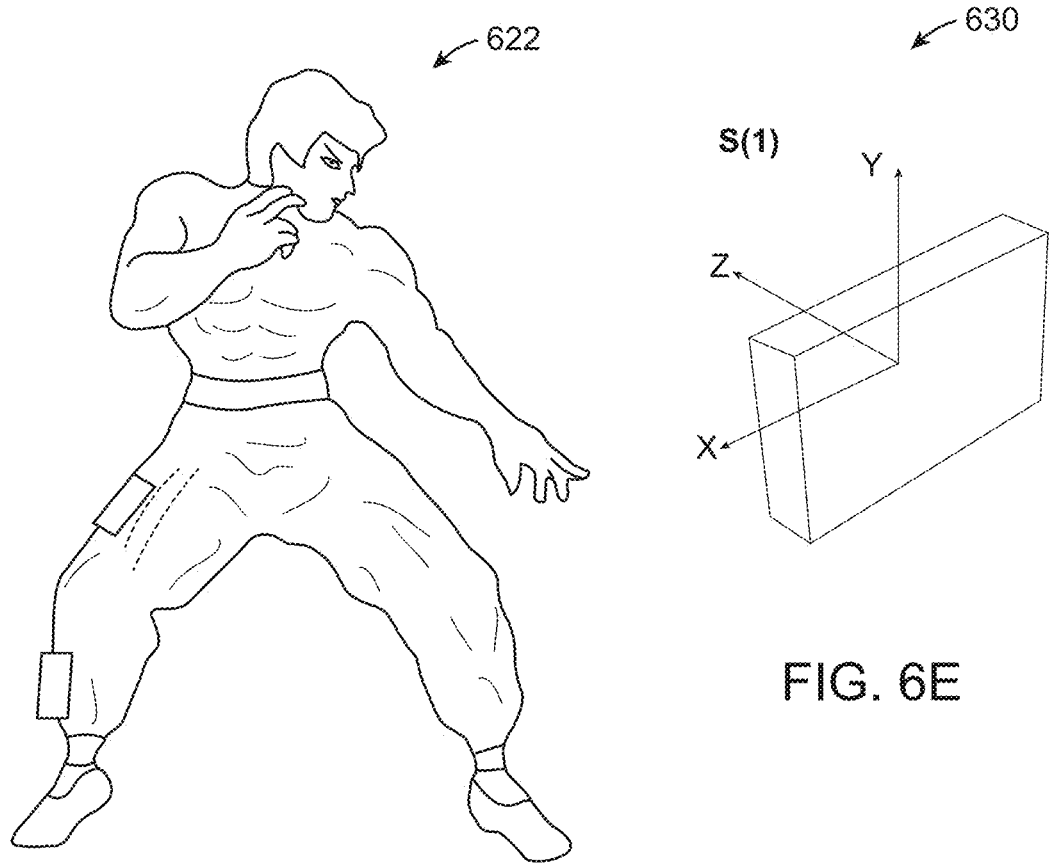
FIG. 6C illustrates an anatomical description of resulting joint calculated based on the two sensors attached onto two different body parts.
FIG. 6E shows an example of anatomical coordinate system created according to one embodiment of the present invention.
Figure 6D:
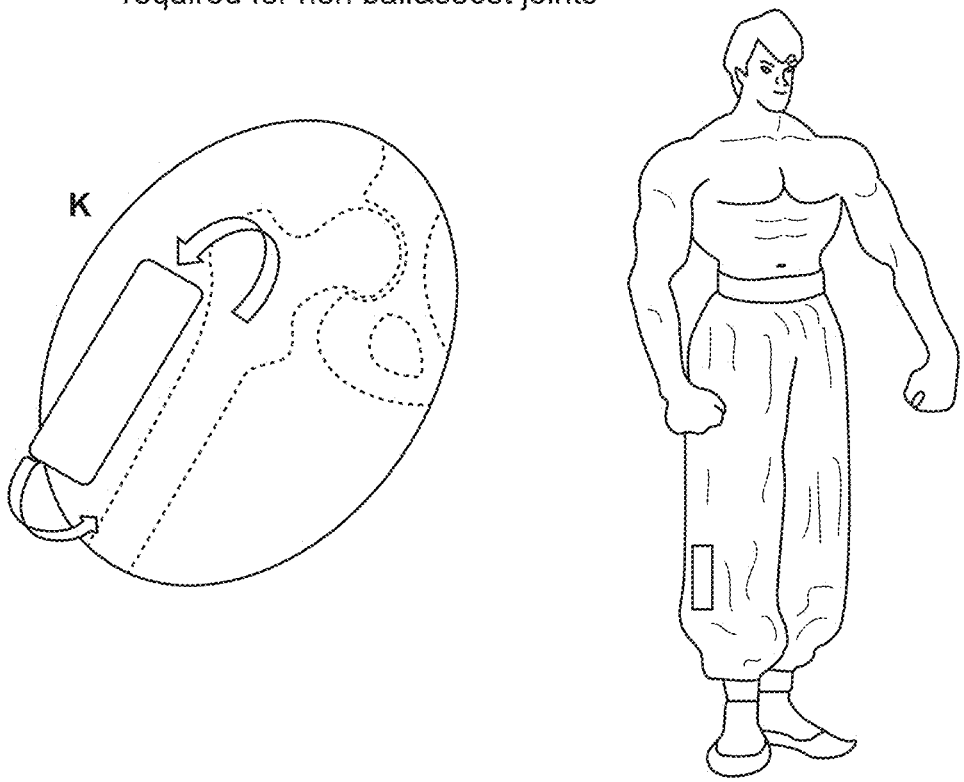
FIG. 6D shows different options to create an aligned anatomical coordinate system.

During calibration, each constant relation is calculated so that each body segment can be a reliable representation of the anatomy behind. The reasons why it is important to implement the anatomical description of joints, instead of simply getting the relative orientation between two probes positioned on the two segments, are multiple. Without the anatomical description, each sensor positioned on the body segment can only provide information regarding the "overall" behavior of the rigid body. In this way, the body segments which are completely different might have the same orientation outputs. Without the anatomical description, the resulting joint calculated from the two sensors orientation will not describe the 3D anatomical rotations. In other words, a knee that has few degrees of rotation would be assumed like it is bull rotating like in a rodeo country simulator as illustrated in FIG. 6C. Therefore, without the anatomical link, it is not possible to explain the signals coming out from the calculations.

The first step in creating the constant relation between a sensor module and a body segment underneath requires the construction of an anatomical coordinate system for the segment. Since the probes do not normally measure body landmarks or specific trajectories, the creation of the anatomical coordinate system may be performed by fusing the sensors data with orientation data, using different methods, such as that shown in FIG. 6D, where it shows different options to create an aligned anatomical coordinate system.

An example of the anatomical coordinate system construction 630 is shown in FIG. 6E, where the vertical anatomical axis (Y) is constructed by means of gravity direction, the medio-lateral or mediolateral anatomical axis (X) is constructed in order to be driven by the vertical direction and the embedded z axis direction is sensed by a sensor positioned on the subject's trunk. The third anatomical axis Z is constructed as a cross product of the first two in order to eventually obtain an orthogonal, right-handed ruled tern of axis. The following equations summarize the relationships.

$$^G y\_trunk = \text{gravity vector}$$

$$^G x\_trunk = ^G z(\text{trunk sensor})\char`\^ ^G y\_trunk$$

$$^G z\_trunk = ^G x\_trunk\char`\^ ^G y\_trunk$$

Thus the anatomical trunk at instant t* during calibration is given by: $^G R_{anat\_tru}(t^*) = [^G x^T, ^G y^T, ^G z^T]$.

The constant relation (from the same instant of calibration) is therefore calculated as follows:

$$^{Anat\_tru} R_{sensor\_tru}(t^*) = K = [^G R_{anat\_tru}(t^*)]^{T*G} R_{sensor\_tru}(t^*);$$

the resulting anatomical coordinate system is represented in FIG. 6E.

Joint Rotation Calculation

The constant relation (from the same instant of calibration) is therefore calculated as follows: each joint of the body (for example the knee) is modeled anatomically starting from the anatomical description provided by the two adjacent segments, a proximal segment (thigh) and a distal segment (shank). The trunk of the body gives the only exception. Although created anatomically, it does not have a proximal joint to consider, therefore it will be here considered as a fictitious joint, where proximal segment is the global coordinate system. The steps used to perform the joint kinematics calculation are described below.

First, at every step t during kick, anatomical orientation of the proximal and distal segments, at step t, are calculated as follows for the knee:

$$^G R_{anat\_thigh}(t) = ^G R_{sensor\_thigh}(t) *^{anat\_thigh} R_{sensor\_thigh}(t^*)$$

$$^G R_{anat\_shank}(t) = ^G R_{sensor\_shank}(t) *^{anat\_shank} R_{sensor\_shank}(t^*)$$

The anatomical orientation of the joint is calculated as relative orientation from the anatomical orientations between the distal and the proximal segments: $^{anat\_thigh} R_{anat\_shank}$ = knee orientation;

3D joint angles of rotation are then calculated by extracting Euler angles from the joint orientation, using a specific Euler sequence, chosen depending on the specific joint and movement to be measured.

Identify Repetitions of Movement

By the automatic analysis of the inertial sensors outputs, repetition of the same kind of movement is extracted and the overall executed task is split into similar parts. This operation is performed by following signal patterns going above or below a specific set of 3 thresholds (high, medium, low) taking into account of the variability of movement in different people, sports and gestures. For example, first, a temporary splitting is performed based on predefined thresholds, so that all repetitions can be overlapped each other, by aligning them in time. The three thresholds may then be recalibrated in order to optimize curves overlapping.

Next, new thresholds are used in order to make a second split, eventually providing a time interval for each repetition of movement. The sensor data used for such splitting can be one of the three angular velocity or acceleration components. The reason why this cannot be performed efficiently on kinematics or orientation data is that low values signals from velocity and acceleration data immediately and reliably correspond to parts of no motion, therefore they are independent from the subsequent movement or variability among people.

Figure 6F:
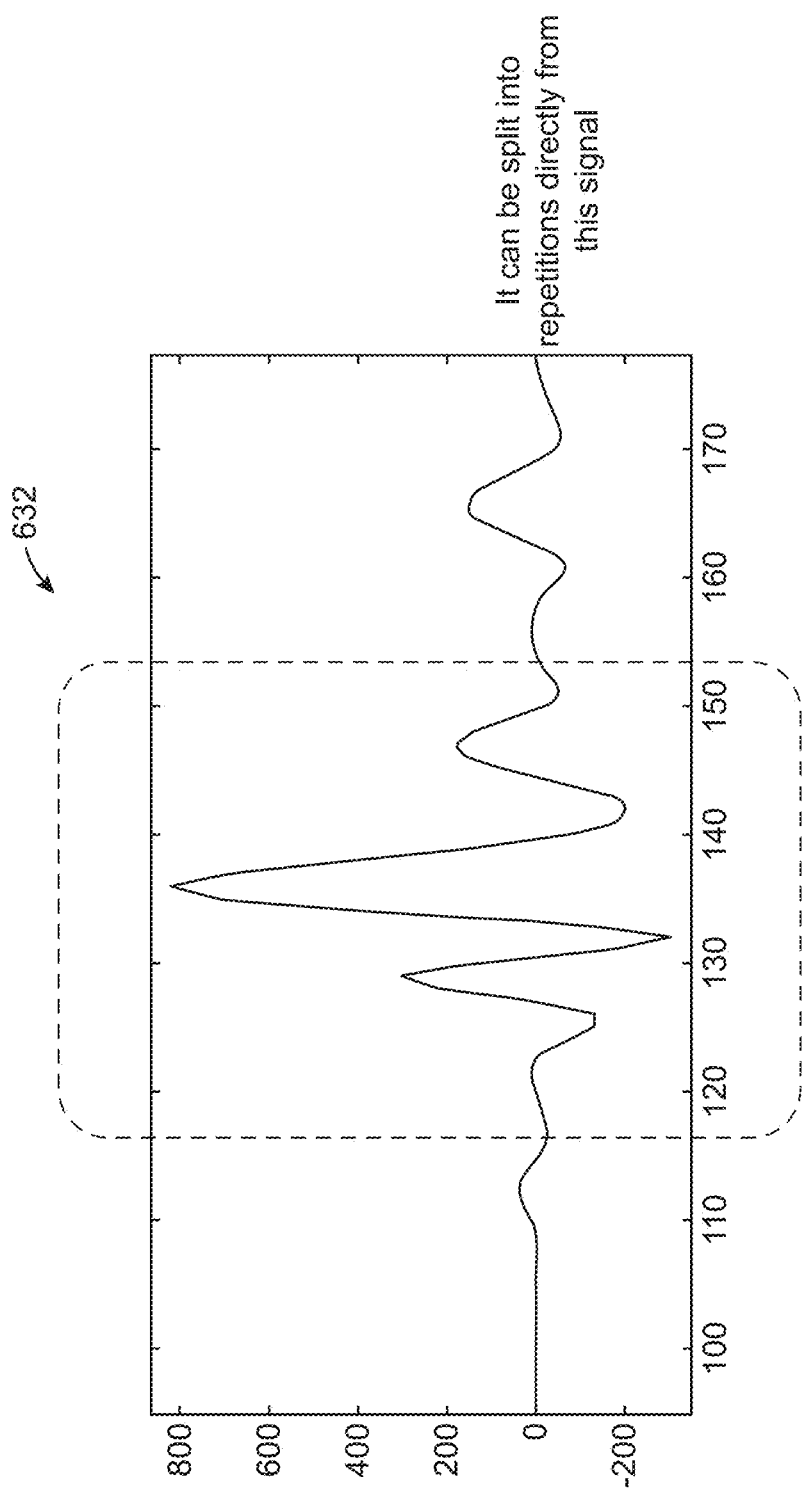
FIG. 6F shows a set of curves to identify the correlation between the speed and joint rotations.

FIG. 6F shows curves 632 to identify the correlation between the speed and joint rotations. The 3D joint rotations and inertial sensors outputs (for example angular velocity of a body segment) can be correlated with each other so that the sign and amplitude of the speed of movement are coupled to a specific joint of the rotation, being therefore a predictor of the motion. This results in movement patterns for each movement repetition, ready to be split into subparts, such as movement phases.

Figure 6G:
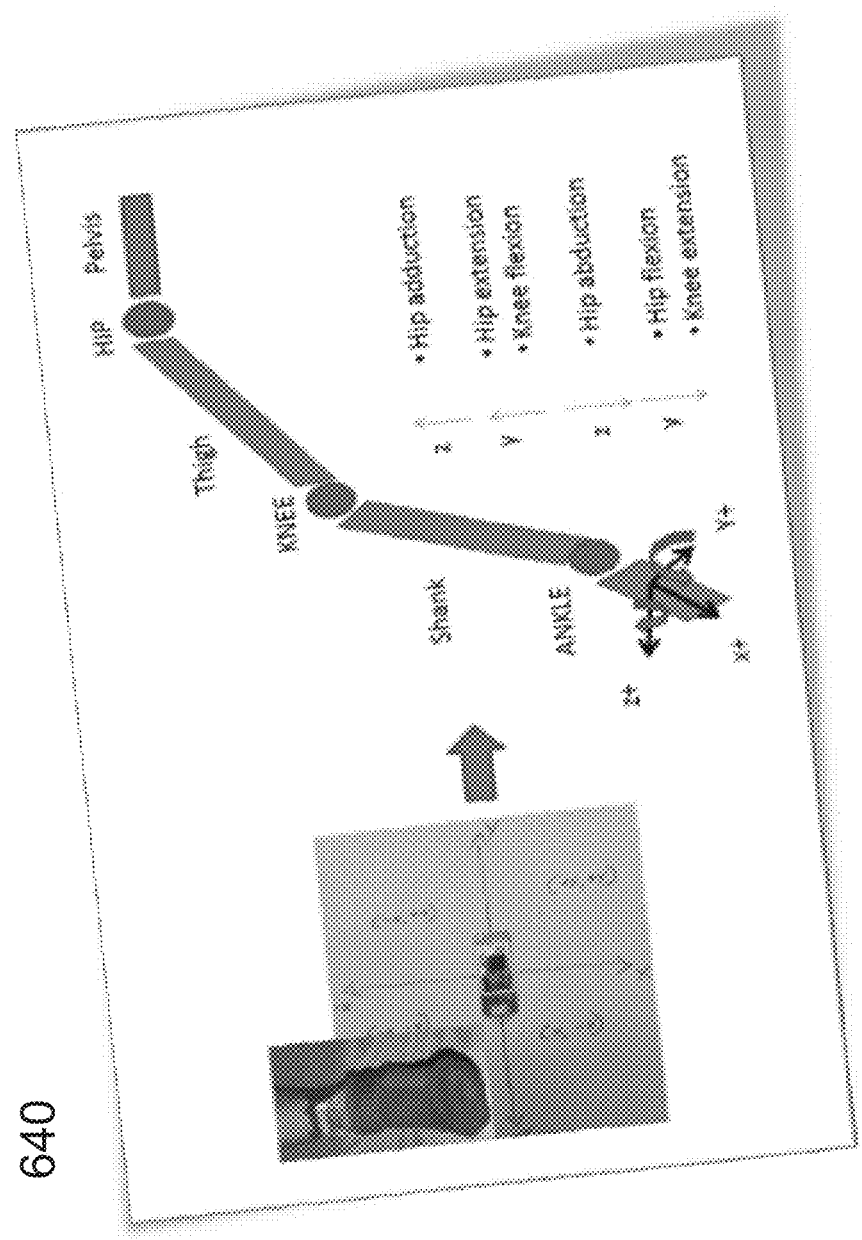
FIG. 6G illustrates how the sensors data is used to split measurement into all the movement repetitions.
Figure 6H:
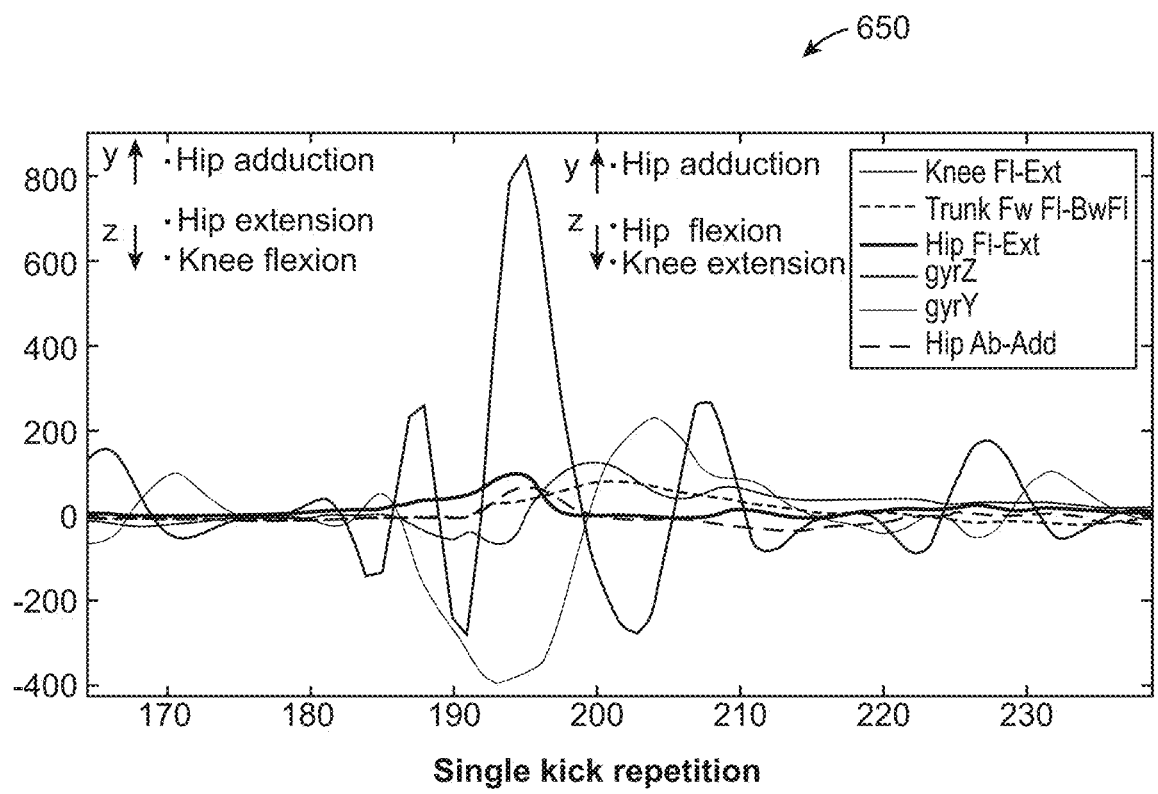
FIG. 6H shows a single repetition interval obtained by means of angular velocity data visualized together with main joint rotations to identify the joint behavior during the interval.
Figure 6I:
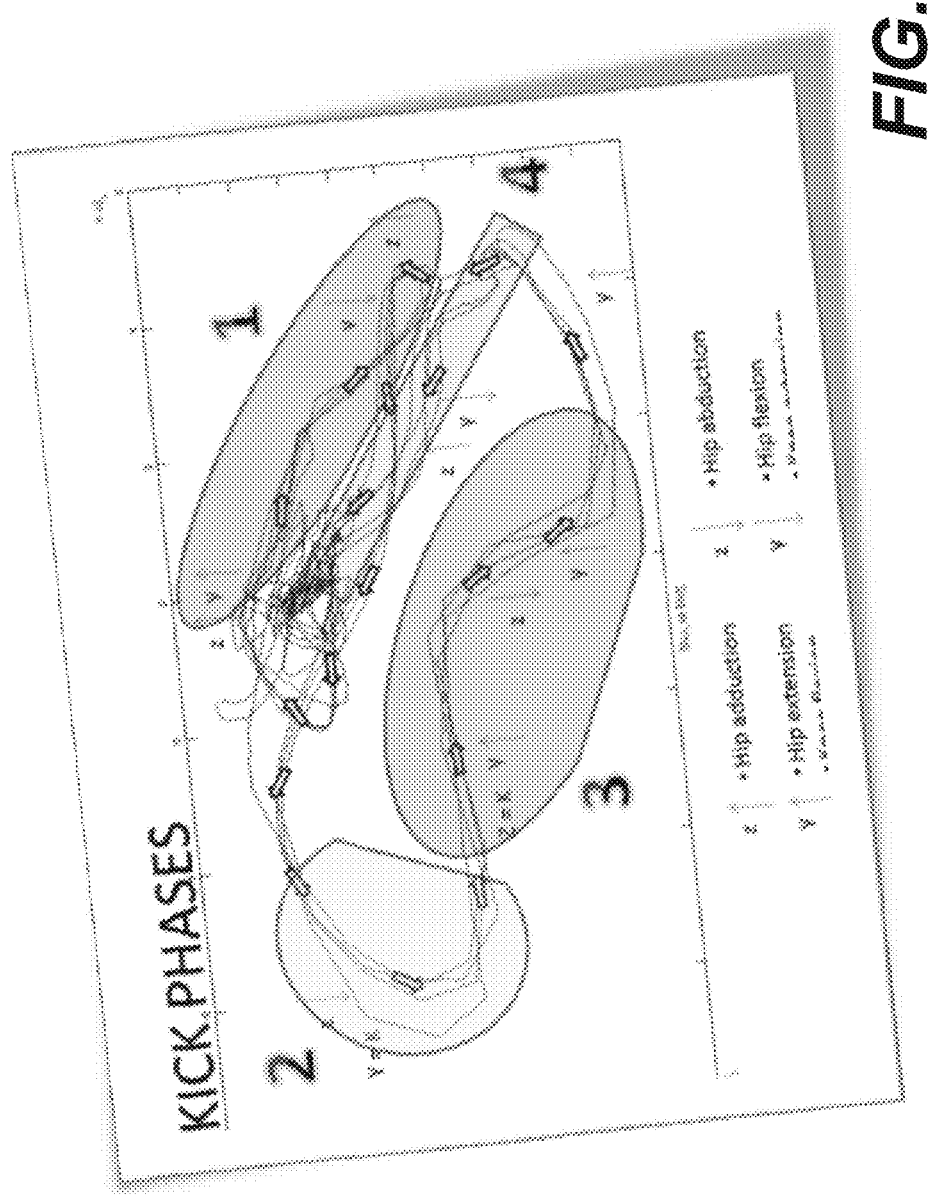
FIG. 6I shows that two components of angular velocity coming from sensors data are correlated with each other in abscissa and ordinate.

FIG. 6G illustrates how the sensors data is used to split measurement into all the movement repetitions. However, the resulting intervals do correspond to the entire movement, not its subparts. Therefore, in order to distinguish among such subparts and make this operation robust enough to detect all subparts in all the repetitions of movement, it is necessary to couple the sensors data information with joint rotations. As shown in FIG. 6H, a single repetition interval obtained by means of angular velocity data, is visualized together with main joint rotations, identifying joint behavior during that interval. In this way, it is possible to split the interval into several subparts, where the entire repetition is this time visualized using a representation independent from time, where 2 components of angular velocity coming from sensors data are correlated with each other in abscissa and ordinate as shown in FIG. 6I.

In the example, Phase 1 corresponds to initial preparation for back spinning kick, being this part linked to hip and trunk small rotations. Phase 2 corresponds to the initial part of the kicking leg swing, while Phase 3 corresponds to the main part of the kick. Phase 4 is the phase where the kicker is returning to his initial position.

Characterization of Movement Phases

Figure 6J:
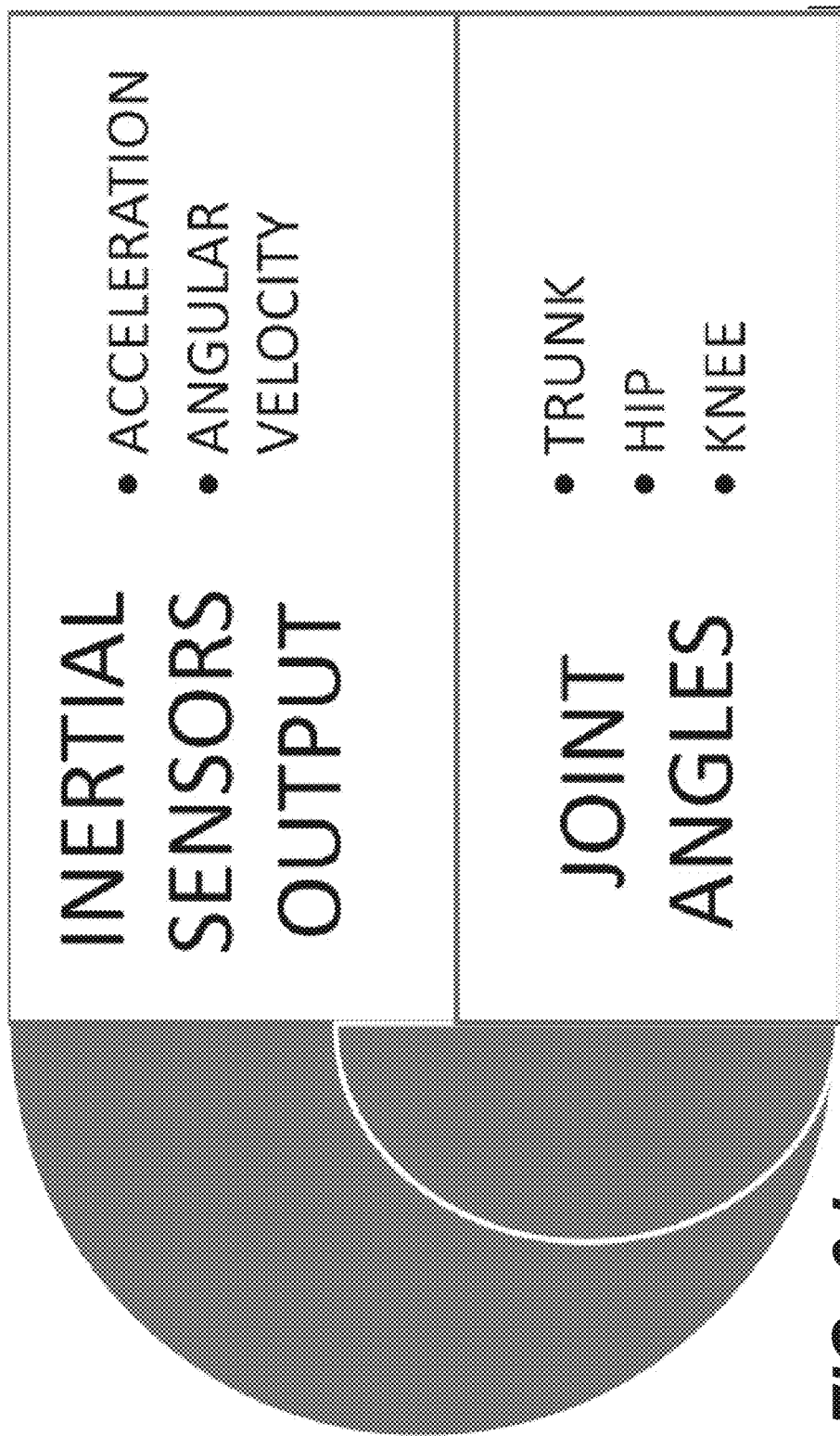
FIG. 6J shows specific parameters can be calculated by comparing correlations between the inertial sensors output and the joint angles, to derive repetition of movement and subparts thereof.

By comparing the above correlations between the inertial sensors output and the joint angles, obtaining repetition of movement and subparts of it, that is the phases, specific parameters can be calculated as shown in FIG. 6J so that such parameters characterize movement within each single phases previously extracted.

FIG. 6K shows an example in which the amount of rotation of trunk between starting posture and loading phase becomes a number characteristic of the initial preparation, while the amount of knee rotation during swinging phase indicates the level of the kick.

Compare Inter-Subject Variability

Figure 6L:
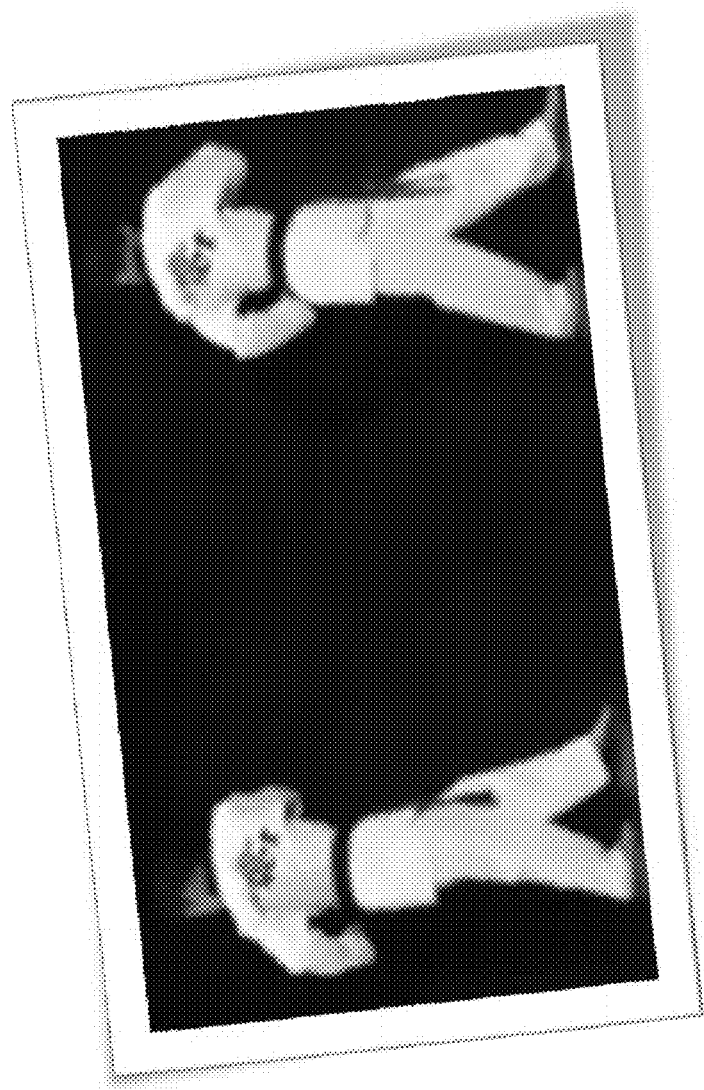
FIG. 6L shows two separate movements made by the same subject (e.g., a single person)

FIG. 6L shows two separate movements made by the same subject. When examining the subject movement with respect to a previous dataset obtained from the same subject, a population or a second subject, parameters previously calculated are finally compared, obtaining as a result how much and in which phase the subject is executing the task differently from the reference.

Figure 6M:
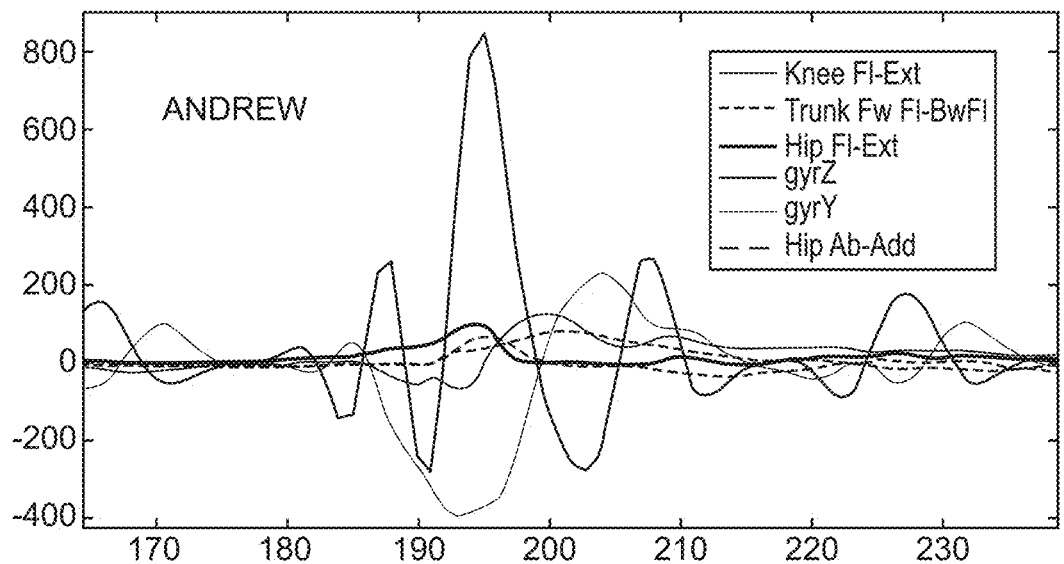
FIG. 6M shows an example of two different subjects sharing similar inertial sensors output pattern.
Figure 6M:
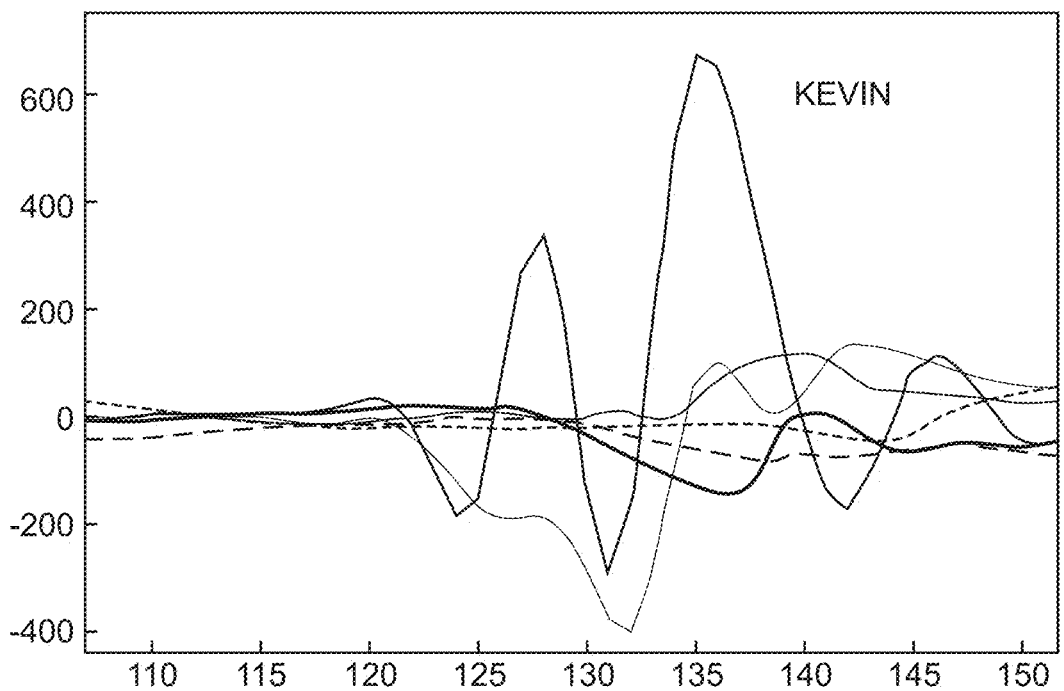

In the example shown in FIG. 6M, two different subjects share similar inertial sensors output pattern, however speed of movement coupled with different behavior at trunk and hip rotations, generated two different kicks which can therefore be characterized, corrected to enhance subject experience or be stored for future use.

Tennis Exemplary Embodiment

For purposes of illustration, an implementation for a tennis application is now described. In this embodiment, the system is configured to: extract movement features from data obtained by in vivo measurement of human body motion tasks using inertial-sensors technology, creating standard ensemble of knowledge around specific motions in tennis and use the above information around specific motions to automatically recognize the type of movement coming from data collected on a new task execution, investigate on its peculiarities, automatically determine the part beyond standard execution of the gesture. The following sections include a short description of algorithms, which can be implemented. Sections are ordered in an exemplary sequence so that each item requires the previous one to be implemented in order to operate correctly.

Figures 7A, 7B:
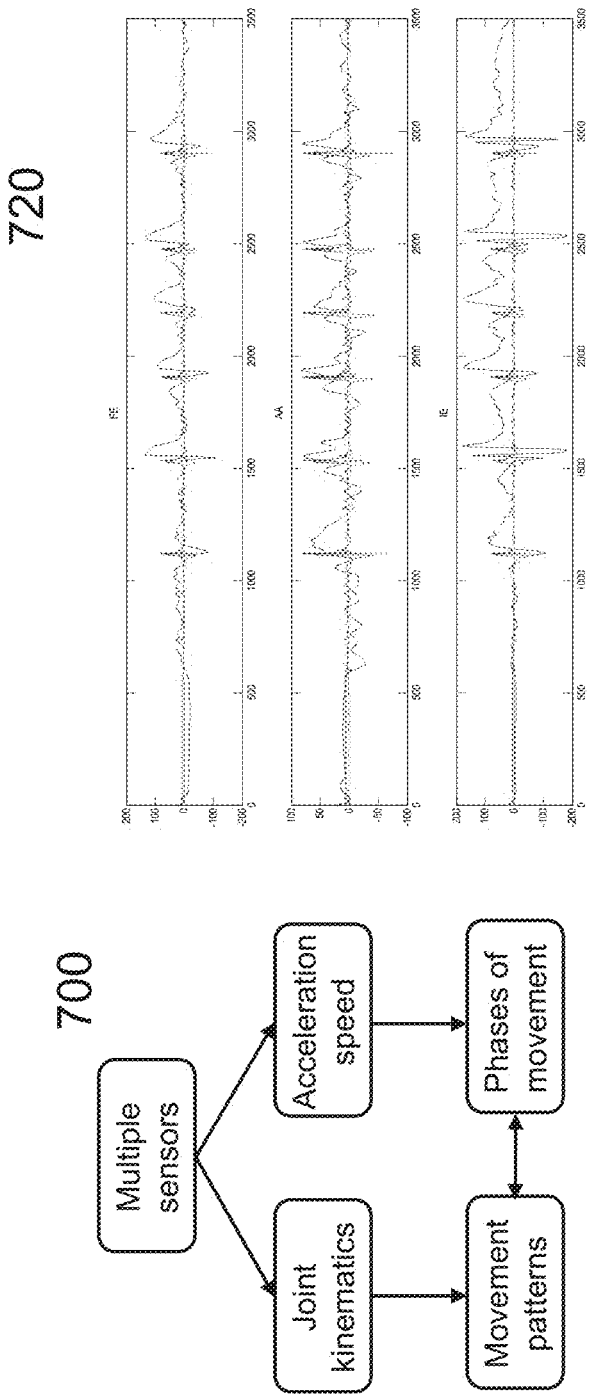
FIG. 7A shows an exemplary kinematic model for movement extraction.
FIG. 7B shows a set of curves, where 6 consecutive ball hits are represented together with the upper arm kinematics, high peaks acceleration are visible for more than one sensor axes.

FIG. 7A shows a kinematic model 700 for movement extraction. Multiple inertial sensors platforms are timely synchronized with each other and attached over different body parts of a tennis player. The exemplary locations include chest, shoulder, upper arm, forearm, hand, right and left thigh, right and left shank, finally the racket. As previously described, different methods may be applied in order to extract joint kinematics of trunk, shoulder, elbow, wrist, hip and knee kinematics, starting from a reference posture. A computing device described above can use the movement patterns based on joint kinematics to identify the specific movement involved. Acceleration and angular velocity of body segments are used in order to split a movement, detecting phases and their alterations.

Algorithm for Detection of Ball Hits 3D acceleration data obtained from motion tracker positioned on the forearm and recording motion during tennis forehand gesture is treated in the following way in order to obtain ball hits events. For example, verification can be done on the 3D acceleration during calibration phase, in order to identify which sensor axis is sensing to ball hit, with respect to the sensor position on the body. For all the dataset available in time, the acceleration measured by the sensor axis identified in the previous step is low-pass filtered using a second-order Butterworth filer, in order to obtain a smooth envelope in the signal. All local maximum values along the signal are marked as a candidate for the ball hit event. A specific threshold may be chosen to be corresponding to 5 g in order discard peaks, which cannot be candidate events. Among the candidate events, a threshold of 8 g is chosen as an example in order to identify all high acceleration peaks along the signal timeline. The threshold can be adapted with respect to the specific subject, by asking to perform forehand gestures at his/her maximum speed of movement before training. All time frames corresponding to the high acceleration peaks are stored and used afterwards in order to split movement into different repetitions.

FIG. 7B shows a set of curves 720, where 6 consecutive ball hits are represented together with the upper arm kinematics, high peaks acceleration are visible for more than one sensor axes. The axis which suffered from the most acceleration is chosen as reference. By using kinematics information signals as shown, a bug delay could be obtained when identifying ball hits events.

Recognition of a Proper Repeatable Stroke Versus Abnormal Stroke

Considering a forehand action as an example, recognition of ball hits can be performed from a different perspective than the detection of impact with the ball. The ball hits can be in fact recognized based on the type of motion that is required to perform the ball hit. The result is a more "functional" recognition of the event, based on what the subject actually did around the event. This method allows to automatically convert measured motion in answers to the following questions: Did the subject hit the ball always with the same range of motion? Was the coordination repeatable among all the repetitions of gesture? Did the event actually occur? In other words, despite of the motion, was the ball missed? (This question in fact cannot be answered by simply searching for the ball hit!)

In order to identify repetitions, motion pattern recognition will be used. A reference pattern constituted by threshold of range of motion at the humero-thoracic joint is constructed for the subject during training, by knowing a priori motion measured. Afterwards, thresholds are used as described in the following algorithm. First, humero-thoracic 3D joint angles are calculated for the entire dataset. Next, humerus flexion-extension angle component Vs time is filtered using a second-order low-pass Butterworth filter. All local maximum values are found along the signal pattern.

A threshold in the signal (typically around 80 degrees) is used in order to collect all peaks that correspond to higher values than the thresholds. Steps 2-4 are then repeated for ab-adduction angle component vs time and internal-external rotation angle component v time by using respectively 70 degrees and 150 degrees as thresholds. The number of peaks above the thresholds found in 4 and 5, for each of the angle component, represents the actual strikes performed by the subject in each of the three planes of movement. From a vector space perspective, the idea is that a 3D motion moving in the $4^{th}$ dimension (i.e. time) is equivalent to a 1D motion moving in the $4^{th}$ time dimension along 1 plane, combined for each plane, like three players in different dimensions hitting the ball. Only if all the three players are moving correctly in their plane, result in 3D will correspond to a correct ball hit.

Figure 7C:
FIG. 7C shows a picture of highlighting a situation in which, among 5 consecutive ball hits, hit number 4 show differences in the pattern and peaks above thresholds reached.
Figure 7C:
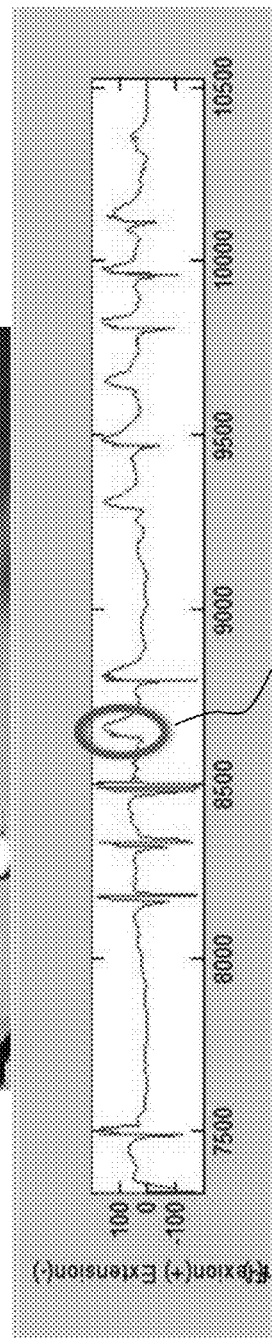

The minimum number of strikes among the 3 groups collected will represent the number of correct strikes, because only a strike correctly occurring in all the three planes will correspond to a correct 3D correct strike. FIG. 7C shows a picture 730 highlighting a situation in which, among 5 consecutive ball hits, hit number 4 show differences in the pattern and peaks above thresholds reached. The number of correct strikes in the plane represented by the signal 732 in the corresponding curve is therefore 4. If the other planes do not show a difference in the pattern among the 5 ball hits, the minimum number of strikes among the three planes will be 4, therefore corresponding to 4 correct strikes.

Algorithms for Repetition Identification

By means of previously calculated ball events, all start and stop events for the movement repetitions are provided. The entire motion is therefore split according to the start and stop events, so that the entire dataset is grouped in as many timeslots vectors as the number of repetitions. All accelerations, angular velocities and joint angles are split according to these groups, obtaining a total of new N dataset where N stays for the number of repetitions.

Number of Steps Detection

Steps detection is applied in a similar way than the ball hits detection. Instead of forearm acceleration data, right and left shank acceleration data are used in order to detect the steps. In one embodiment, verification is done on the 3D acceleration coming from right and shank sensors during calibration phase, in order to identify which sensor axis is sensing jump/vertical motion, with respect to the sensor position on the body. For all the dataset available in time, the acceleration measured by the sensor axis on the right or left shank identified in the previous step is low-pass filtered using a second-order butterworth filer, in order to obtain a smooth envelope in the signal. All local maximum values along the signal are marked as candidate for ball hit event. A specific threshold is chosen discard peaks that cannot be candidate events. Among the candidate events, a threshold of 2 g is chosen as an example in order to identify all steps acceleration peaks along the signal timeline. The threshold can be adapted with respect to the specific subject, by asking to perform steps on site before training. All time frames corresponding to the high acceleration peaks can be stored and used to count the total number of steps along the measurement. The number of steps between each repetition and the next is counted based on previously calculated time frames that corresponded to ball hits (therefore start/end of a repetition). The same may be applied both for right and left side.

Strike Zone Analysis

In order to evaluate if the ball was hit with body parts moving inside of the strike zone, the following steps may be carried out. These steps may be performed so that strike zone is not anymore considered only a matter of height, but how this height is actually reached by the subject.

First, given joint angles split according to N dataset, where N stays for the number of repetitions. Hip flexion value is calculated at ball hit time, inside of each of the N groups. Step 2 is repeated for the knee joint. Step 2 is repeated for the shoulder joint. Steps 2, 3, and 4 are performed both for right and left side. Shoulder, Elbow, Wrist, Racket height is estimated during all the repetitions of movement, by using the algorithm described below.

Figure 7D:
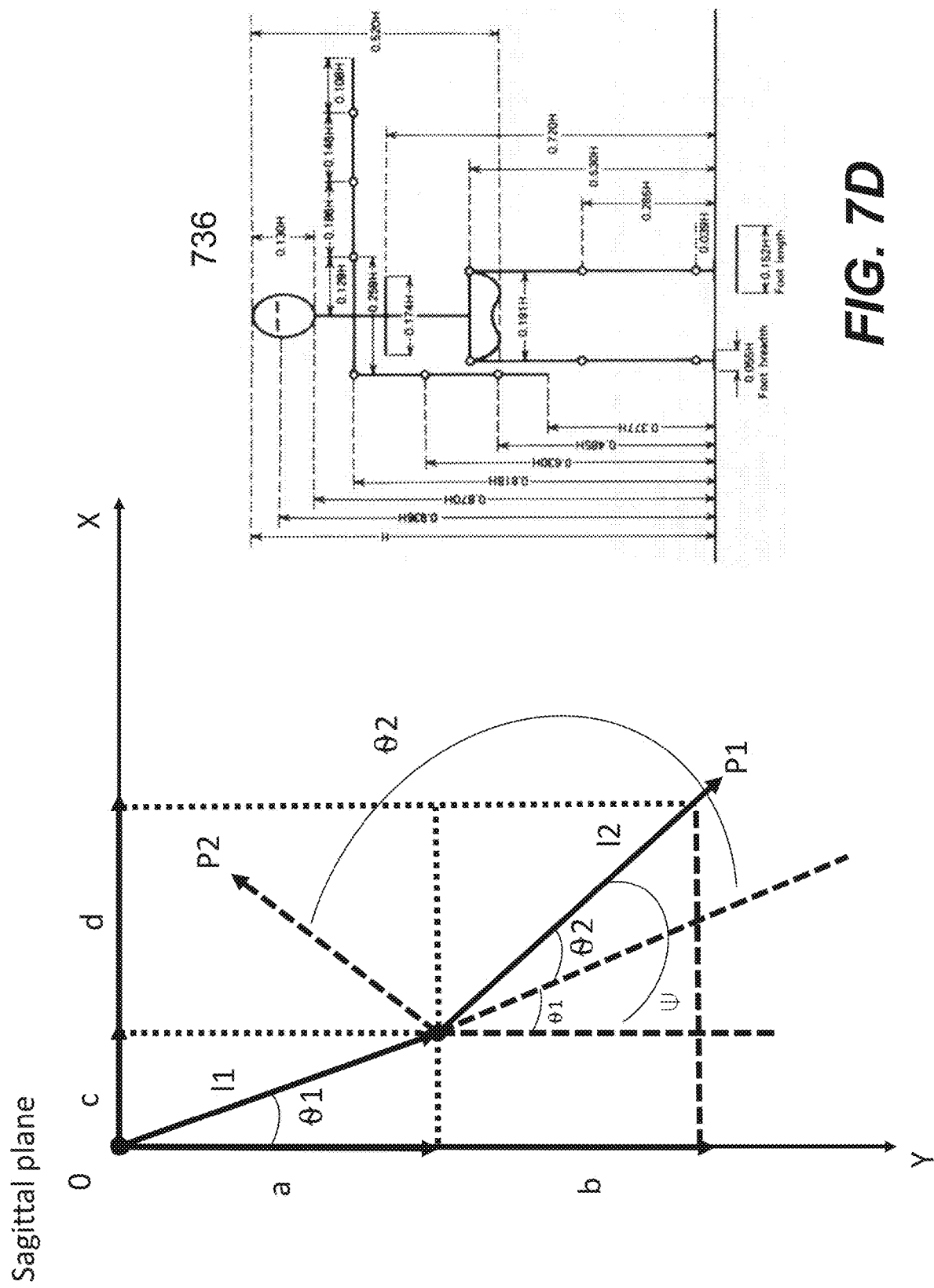
FIG. 7D shows an example of a ball assumed to be hit at the racket tip of the tennis player.

Information coming from steps 1 to 5 will provide information regarding the correctness of the movement, in terms of proper motion pattern. If Step 7 did not result in an acceptable pattern, ball height will not be estimated. If Step 7 provided an acceptable pattern, ball height will be estimated to understand if the acceptable pattern occurred within the strike zone. Ball height through direct kinematics:

height=152.3999951232+22.85999926848; % cm Joe
l1=0.186*height % upperarm
l2=0.146*height % forearm
l3=0.108*height % hand
l4=68.5799978054401% cm racket 27"
% sagittal plane
% settings theta values
theta1=ht.FE*pi/180;
theta2=elbow.FE*pi/180;
theta3=wrist. FE*pi/180;
theta4=0; % angle between hand and racket is assumed/to be zero FIG. 7D shows an example of a ball assumed to be hit at the racket tip of the tennis player. In one embodiment, a two (2D) direct kinematics model may be created starting from player shoulder as origin of a Cartesian plane. One Cartesian plane is constructed for the sagittal plane motion of the player and the frontal plane motion, therefore providing a double 2D model.

As for the application of direct kinematics concept, the main input of the model in each plane will correspond to anthropometric parameters coming from the player (in this example the subject's height) and the joint angles for humero-thoracic, elbow and wrist joint, taking only the component involved in the selected plane. For example, for the sagittal plane, the model will use as input the humero-thoracic flexion-extension angle, the elbow flexion-extension angle, the wrist flexion-extension angle.

The reason for iterating the algorithm for the two different planes is to split forehand motion from 3-dimensional to 2 dimensions, therefore studying separately the expected main pattern of motion in the sagittal plane and the secondary pattern of motion in the frontal plane. Variations in each of these planes will automatically correspond in a variation in the other plane, allowing to split variability in motion due to the use of one plane with respect to the other.

The following steps may then be used in order to calculate ball height: assuming X is the direction forward with respect to the body, pointing forward is positive, while Y is the vertical direction pointing down, the origin is corresponding to the shoulder joint center:

Trajectory of elbow can be calculated as follows:
oEx_sag=l1*sin(theta1); % position of elbow along x axis
oEy_sag=l1*cos(theta1); % position of elbow along y axis
where l1 is the length of the upper arm derived from the subject's height and anthropometric tables from Woltring, 1990 and theta1 is the humero-thoracic angle component of flexion-extension expressed in radians.

Trajectory of Wrist Can be Calculated as Follows:
oWx_sag=oEx_sag+l2*sin(theta1+theta2); % position of wrist along x axis
oWy_sag=oEy_sag+l2*cos(theta1+theta2); % position of wrist along y axis
where l2 is the length of the forearm derived from the subject's height and anthropometric tables from Woltring, 1990 and theta2 is the elbow angle component of flexion-extension expressed in radians.

In a similar way, trajectory of the interface between hand and the racket can be calculated as follows:
oFx_sag=oWx_sag+l3*sin(theta1+theta2+theta3); % position of interface between hand and racket along x axis
oFy_sag=oWy_sag+l3*cos(theta1+theta2+theta3); % position of interface between hand and racket along y axis
where l3 is the length of the hand derived from the subject's height and anthropometric tables from Woltring, 1990 and theta3 is the wrist angle component of flexion-extension expressed in radians.

In a similar way, trajectory of the racket can be calculated as follows:
oRx_sag=oFx_sag+l4*sin(theta1+theta2+theta3+theta4); % position of racket along x axis;
oRy_sag=oFy_sag+l4*cos(theta1+theta2+theta3+theta4);
% position of racket along y axis;
where l4 is the length of the racket derived from its geometry and theta4 is the angle component of flexion-extension of the racket expressed in radians. If the racket is assumed to not move with respect to the hand, theta4=0.

In some embodiments, initial signal offsets can be removed as follows: % removing offset from measurements
for i=1: length(oEx_sag)
  oEx_sag(i)=oEx_sag(i)−oEx_sag(1);
  oEy_sag(i)=oEy_sag(i)−oEy_sag(1);
  oWx_sag(i)=oWx_sag(i)−oWx_sag(1);
  oWy_sag(i)=oWy_sag(i)−oWy_sag(1);
  oFx_sag(i)=oFx_sag(i)−oFx_sag(1);
  oFy_sag(i)=oFy_sag(i)−oFy_sag(1);

oRx_sag(i)=oRx_sag(i)−oRx_sag(1);
oRy_sag(i)=oRy_sag(i)−oRy_sag(1); end.

Figure 7E:
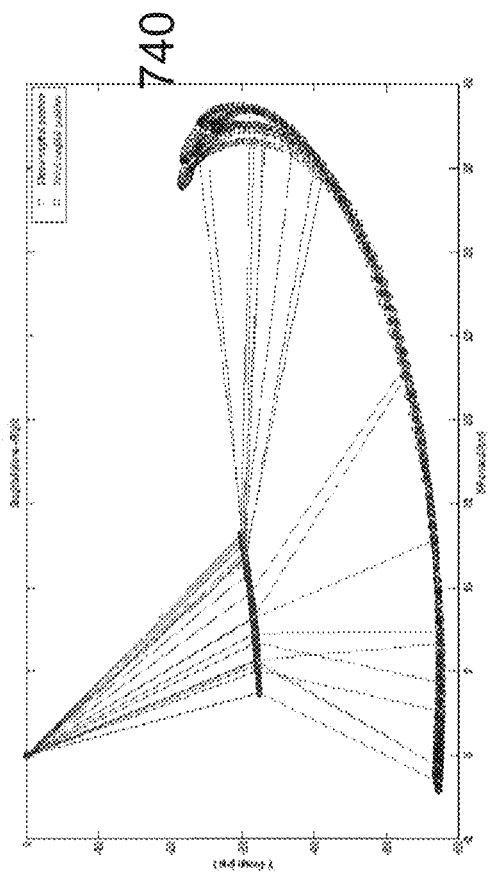
FIG. 7E shows an example of trajectory estimate of elbow and wrist for a simple elbow flexion task in the sagittal plane.

An estimate of the inner static error in the method for the specific subject (which can be used as tolerance to the user) can be obtained first by calculating all the above variables during a calibration step where the subject is keeping all arm and racket vertically. Then, by comparing the maximum values reached by all the joints with respect to the origin in all directions with the sum of the length of the segments included between the origin and the joint. For example in the case of the elbow, error estimate of the elbow height can be calculated as follows: l1−max(oEy_sag). An example of resulting trajectory estimate of elbow and wrist is provided in the picture for a simple elbow flexion task in the sagittal plane as shown in FIG. 7E.

Steps 1-7 are repeated in a similar way considering a frontal plane. Assuming X is this time the direction lateral with respect to the body, pointing right is positive, while Y is again the vertical direction pointing down, the origin is again corresponding to the shoulder joint center. Theta1, 2, and 3 are this time corresponding to the second angle component of the joint angles previously calculated from 3D kinematics algorithm, that is respectively humero-thoracic ab-adduction, elbow ab-adduction, wrist ab-adduction.

Figure 7F:
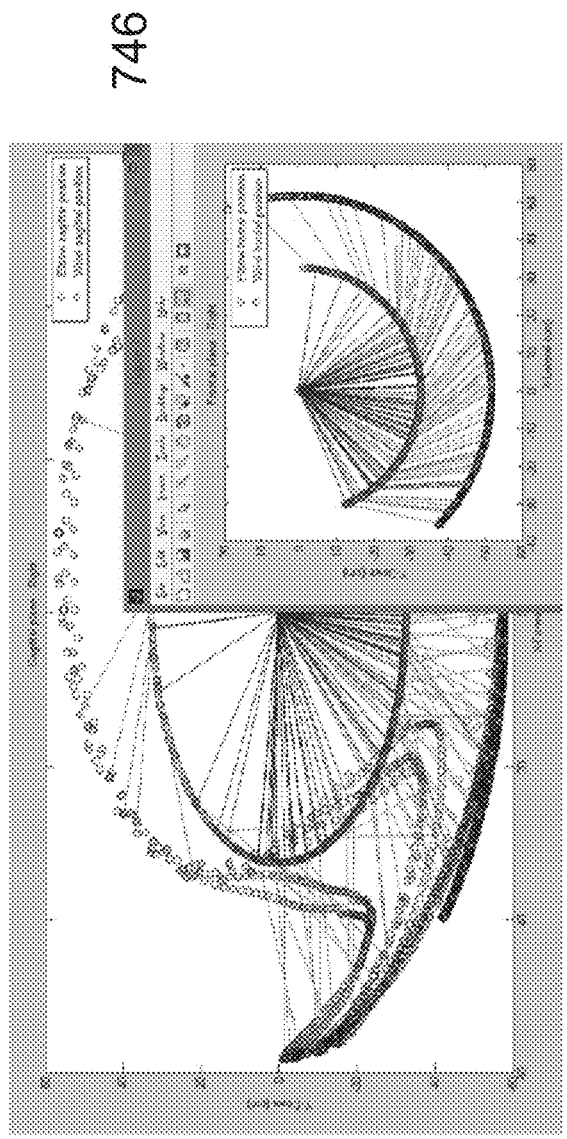
FIG. 7F shows both sagittal and frontal plane trajectories of elbow and wrist joint during a tennis serve movement.
Figure 7G:
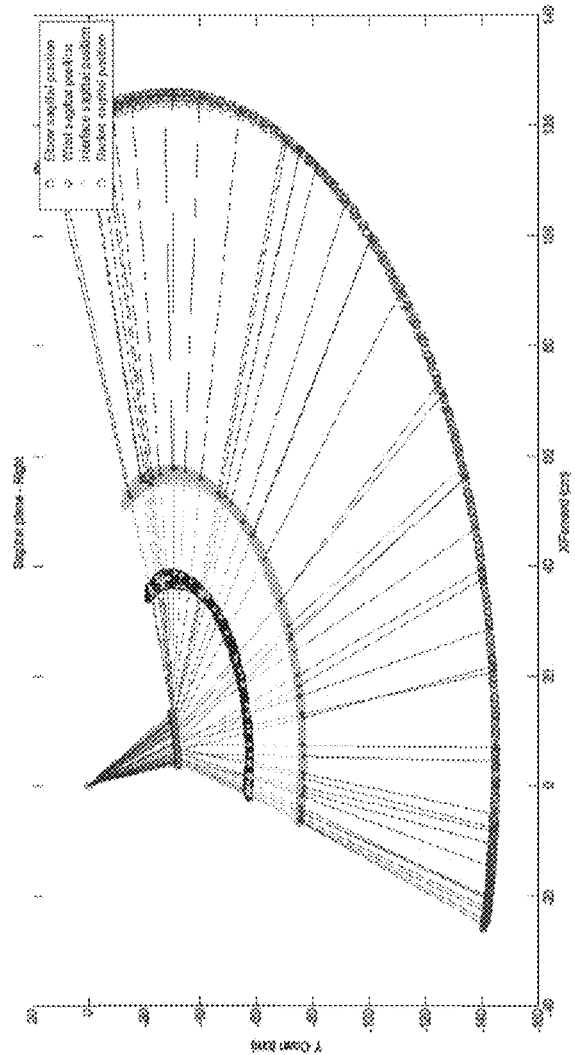
FIG. 7G and FIG. 7H show additional examples where wrist and racket trajectories are also estimated.
Figure 7H:
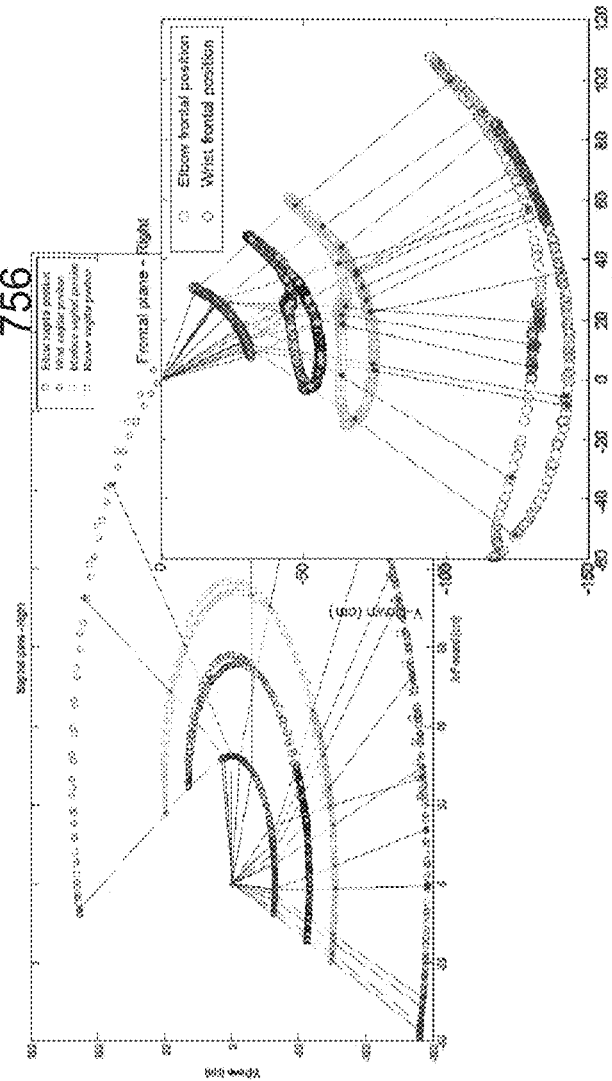

Maximum and minimum values in the trajectories obtained in the sagittal and frontal planes are used in order to generate a 3D parallelepiped which will correspond to the maximum range that the player has reached. The values of the trajectories reached at the ball hit time, as described in Section 2, will represent the actual height reached by joint within the 3D parallelepiped. FIG. 7F shows both sagittal and frontal plane trajectories of elbow and wrist joint, during a tennis serve movement. FIG. 7G and FIG. 7H show additional examples where wrist and racket trajectories are also estimated.

Exemplary Motion Detection Algorithms

Figure 7J:
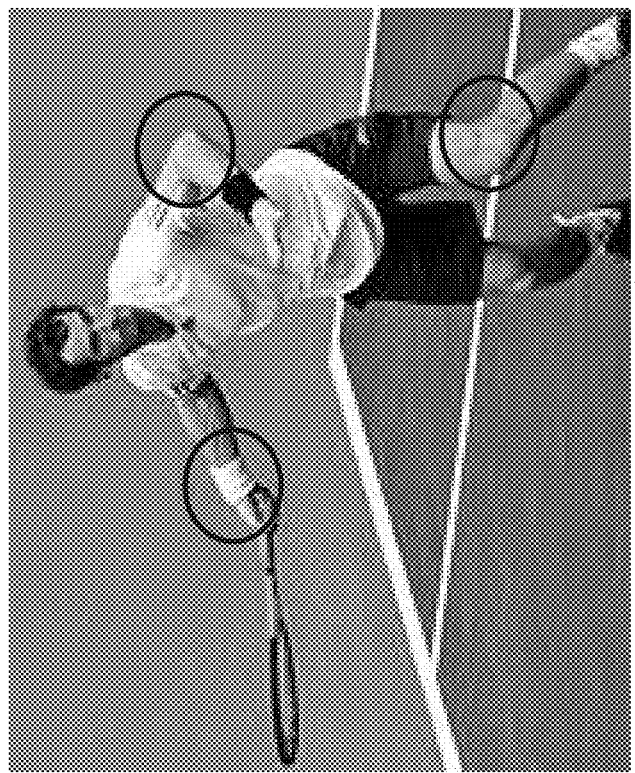
FIG. 7J shows an example of characterization works globally by analyzing several parts of the body together.
Figure 7I:
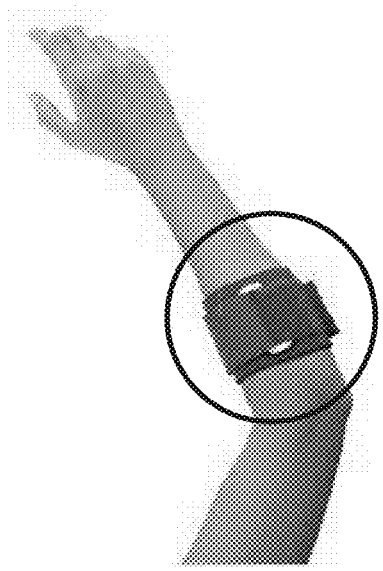
FIG. 7I shows an example in which an arm wearing a sensor module.

Motion detection algorithms may be employed for identifying with a certain confidence, what type of motion (among a pre-defined list) the wearable technology is measuring on a specific subject. A number of variables can be involved within the definition and development of such algorithms for the automatic recognition of the motion:

Type of movement: static posture, simple movement, complex action related to a specific sport, quick motion in-between two similar actions, quick motion in between two different actions Sub-type of movement: a complex motion can be performed in N different ways by the tennis player, however among them, there are M different ways where M<N that the tennis player is targeting Intra-player variability, including:
biological variability
scenario/day variability
variability due to muscle fatigue/injury
variability due to learning effect by the player
variability due to speed of execution
variability due to the type of motion Inter-player variability, including:
variability in the execution of the technique
variability due to speed of execution
variability due to type and gender
variability due to the type of motion One way to be able to distinguish among the above variability factors is to perform a two-parallel ways analysis. Motion event detection allows for reducing the number of possible motions to the minimum ensemble that can correspond to the real ones. For instance, volley and tennis serve can be both related to the identification of a swing at height, however they cannot be in the same ensemble of a lateral forehand. The machine running on such screening is able to distinguish among type of motions but not able to distinguish among the same motion repeated in different ways due to an increasing fatigue in the player. This screening works locally on a certain part of the body. FIG. 7I shows an example in which an arm wearing a sensor module.

Motion Characterization.

If the player is flexing the elbow 40 degrees, this can occur during many different types of motion. Therefore this value is not representative of a specific motion. However, while motion detection screening would not look for such variation in the elbow, the motion detection characterization helps to determine the way in which the motion detected in the above motion event detection was performed. In this way two tennis serves executed apparently in the same way locally, or globally show a difference that is due to the variability in the technique execution. This characterization works globally by analyzing several parts of the body together as shown in FIG. 7J.

Both the above parallel ways are focused on a 3-dimensional analysis or, better, on a 4-dimensional analysis where time is the $4^{th}$ dimension. This is because the motion pattern recognition can identify a motion not frame-by-frame but only within a certain "window" of data frames which include the motion itself.

Motion Detection Parameters

The method 1) and 2) described so far can be applied in a sequence or work together in order to calculate:

the beginning and ending of a certain motion a specific time event within the motion, for example a certain contact or impact all inertial properties occurring within the motion (e.g., acceleration, rate of turn)

all kinematics properties (e.g., joint rotations at shoulder, elbow, wrist, chest, during the execution of a forehand)

based on previously described algorithm and the above kinematics, measurement of X, Y position of joints on an anatomical plane during the motion quality indicator for a specific gesture. For example, in the case of a forehand action, by crossing information regarding the trajectory estimation of the ball with the joint rotational data, it is possible to track the "strike zone" inside of which a correctly executed of the forehand action needs to operate injury indicator for a specific gesture. All injury indicators are based on the value reached by variables overcoming certain thresholds that are defined based on a reference. For example, the level of elbow flexion=0 degrees should not be overcome at the ball contact event.

Event Detection Algorithms

The algorithms created for the detection of specific features belonging to a certain motion will be referred here as SEDA algorithms (Shots Event Detection Algorithms). Here below is an example related to the use of SEDA1 and SEDA2 algorithms:

SEDA1 is the first level of event detection algorithm and is based on the pattern identification of the X axis measured by a 3D gyroscope positioned at the wrist level of the tennis player, where the X axis is the axis along the length of the forearm. SEDA1 is able to provide starting and ending frames of forehand, backhand, overhead.

Figure 8A:
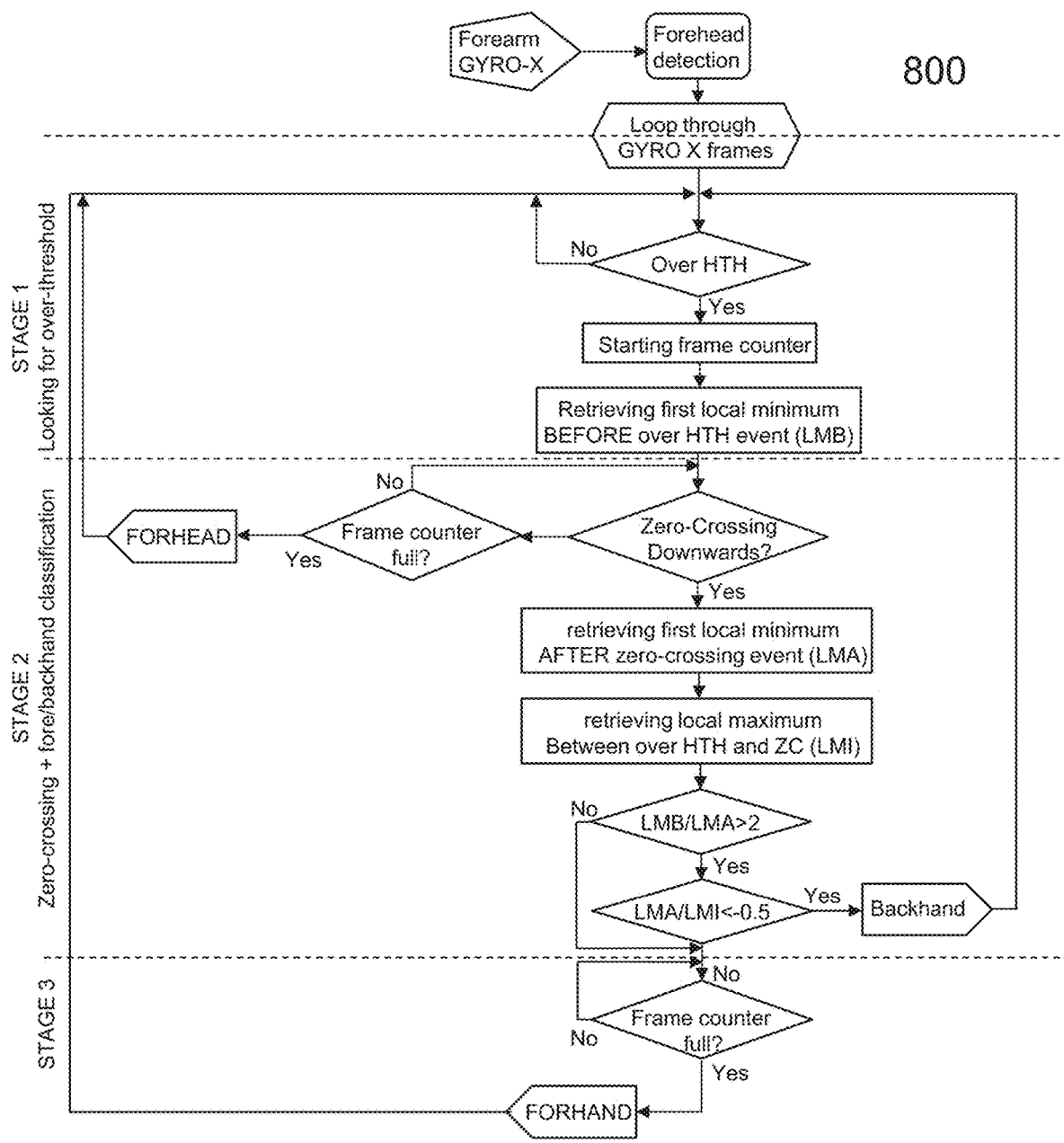
FIG. 8A shows a flowchart regarding the application of SEDA1 algorithm on forehand analysis, wherein SEDA1 provides high confidence in the identification of forehand motions.

FIG. 8A shows a flowchart regarding the application of SEDA1 algorithm on forehand analysis is provided. SEDA1 provide high confidence in the identification of forehand motions. SEDA2 is a second level of event detection algorithm and it operates in a similar way than SEDA1. However, SEDA2 is created in order to increase the probability of identifying backhand and overhead shots.

SEDA2 is based on the pattern identification of the Y and Z axis measured by a 3D gyroscope positioned at the wrist level of the tennis player, where the X axis is the axis along the length of the forearm, Z axis is pointing towards the inner of the gyroscope.

SEDA1 is able to provide starting and ending frames of backhand and overhead shots.

SEDA3 is the third level of event detection algorithm and it operates in a different way than SEDA1 and SEDA2. The latter algorithms use gyroscope signal as measurement input, while SEDA3 operates on joint kinematics information calculated as described in Chapter 6. An example of SEDA3 application regarding forehand analysis is based on the following concept:

Although elbow joint is strongly related to the execution of a forehand action, the range of motion regarding its flexion is not characteristic of certain forehand phase but rather an indication of the correct execution of it.

However, again for the elbow, if the tennis player is not a beginner, elbow prono-supination angle is characteristic of the moment of preparation to the hit and the ending of the forehand In other words, the same forehand can occur with more than 100 degrees (combination) of elbow flexion, but much less combinations of prono-supination angles Therefore, in a similar way as in SEDA1 and 2, high and low thresholds on the prono-supination angles can be used in order to identify starting and ending phases of forehand.

In one embodiment, while SEDA1 and SEDA 2 can determine the ball contact event by means of changes in speed.

Classifier and Confidence Level

Feature detection algorithms work on different signals at once. For this reason, their output needs to be analyzed and weighted by a classifier machine which at the end of the process returns, for each motion analyzed, the percentage of confidence of the resulting classification of type, sub-type, quality and risk level of the motion. This can be of great value especially when it is required to analyze multiple motions, multiple movement repetitions or multiple subjects executing the same motion.

An example of classifier based on SEDA1 and SEDA2 algorithm output is here described. Steps involved in the classifier are:

Application of SEDA1 based on X axis gyroscope data
Application of SEDA2 based on Y and Z axes gyroscope data
Assembling arrays of identified forehand, backhand, overhead motions
An overlapping window is defined by which, for each forehand time interval found by SEDA1, the algorithm detects if any backhands or overhead motions were found by SEDA2 and so on, until a complete mapping is created
A classifier weight is therefore assigned to each type of motion and a classification is presented An example of classifier that analyzes and weights results produced by SEDA1 and SEDA2 algorithms is provided here together with the confidence levels reached. It must be noticed that, without information regarding the way and coordination in which the specific motion is executed, the confidence level is not increased.

```
OUTPUT EXAMPLE 1
[SEC1] No forehands detected in file
[SEC1] Single BACK from S2 at frame 778
[SEC1] Single BACK from S2 at frame 1185
[SEC1] Single BACK from S2 at frame 1552
[SEC1] Single BACK from S2 at frame 1941
[SEC1] Single BACK from S2 at frame 2406
[SEC1] Single BACK from S2 at frame 2800
[SEC1] No overheads in file
[SEC1] -- End of classification --
[SEC1] CONFIDENCE ANALYSIS:
[SEC1] Total number of unique shots: 6
0 1 0
0 1 0
0 1 0
0 1 0
0 1 0
0 1 0
[SEC1] Classification confidence %
- BACK at frame 778-100%
- BACK at frame 1185-100%
- BACK at frame 1552-100%
- BACK at frame 1941-100%
- BACK at frame 2406-100%
- BACK at frame 2800-100%
OUTPUT EXAMPLE 2 on match
[SEC1] Overlapping shot (Fore->Over) found at:
S1.FORE >> 2341 || S2.OVER >> 2360
[SEC1] No overlaps found for FORE data
[SEC1] No overlaps found for FORE data
[SEC1] No overlaps found for FORE data
[SEC1] Overlapping shot (Fore->Over) found at:
S1.FORE >> 7175 || S2.OVER >> 7178
[SEC1] Overlapping shot (Fore->Over) found at:
S1.FORE >> 7650 || S2.OVER >> 7653
[SEC1] Single BACK from S2 at frame 6332
[SEC1] Overlapping shot (Over->Over) found at:
S1.OVER >> 9538 || S2.OVER >> 9553
[SEC1] Overlapping shot (Over->Back) found at:
S1.OVER >> 10860 || S2.BACK >> 10855
[SEC1] -- End of classification --
[SEC1] CONFIDENCE ANALYSIS:
[SEC1] Total number of unique shots: 9
0        1.0000 0
1.0000 0        0
1.0000 0        0
1.0000 0        0
0.5000 0        0.5000
0.5000 0        0.5000
0.5000 0        0.5000
0        0.5000 0.5000
0        0      1.0000
[SEC1] Classification confidence %
- BACK at frame 6332-100%
- FORE at frame 4974-100%
- FORE at frame 5542-100%
- FORE at frame 6772-100%
- FORE at frame 2341-50%
- OVER at frame 2360-50%
- FORE at frame 7175-50%
- OVER at frame 7178-50%
- FORE at frame 7650-50%
- OVER at frame 7653-50%
- BACK at frame 10855-50%
- OVER at frame 10855-50%
- OVER at frame 9538-100%
```

When SEDA3 algorithm output is included in the classifier, confidence level can therefore increase.

Phases and Dimensions

As previously described, acceleration and angular velocity of body segments are used locally in order to split movement. An automatic machine previously described is able to use movement patterns based on joint kinematics to identify the specific movement involved, therefore detecting the beginning and end of each phase and their alterations.

FIG. 8B shows a schematic representation of a recognized motion by SEDA1 and SEDA2, where the start and end of motion are visible together with the ball hit event and specific features which are obtained from the detected motion. When SEDA3 is applied, the ensemble of parameters which characterize the entire motion increases in the sense that is possible to identify which parts of the body are varying within the interval [start gesture, end of gesture]. The identification of the ball event that by definition is within the above interval, allows automatically to separate the entire motion into two different phases, one before the hit and the other after the hit.

All the parameters that are averaged along the time interval, can be recalculated for each of the two intervals identified by the two phases. However, each phase can be further described and split into sub-phases by means of an event different from the ball hit as shown in FIG. 8C. For example, the phase before the hit contains not only the preparation phase for the gesture but also the phase just before the hit.

As it can be normally verified in training settings, there can be some part of these phases which contribute positively or negative to the execution of the gesture. This can be explained by the fact that, for each sub-phase f it is possible to identify a certain number of variables (inertial or kinematics) which contain a variability v which can differ for each sub-phase and/or repetition of movement. It must be noticed that each sub-phase is also characterized by a timeline t.

Therefore, while the local analysis around the ball hit is a 4-dimensional analysis, when the correctness of motion needs to be identified, the number of dimensions becomes 4*f. A certain motion can therefore be characterized by N parameters calculated within 4*f dimensions.

User Interface Tennis Application

The embodiments may thus provide the following features alone or in combination:
  Translating complex technology and database into a very simple-to-interpret interface;
  Pivot chart to simplify complex database representation to the users;
  Connecting the chart to the 3D animation and chart manipulation for easy visualization; and
  Virtual product placement for embedded marketing for monetization.

The embodiments may thus provide the following features alone or in combination. The embodiments may use an easy to use UI to translate these very complex technology and database and present them into a very simple-to-interpret interface. There are several concepts that enhance the user's experience:
  1. Clarity: Simple, clean, and streamlined design
  2. Familiarity: Clear icons with good metaphors
  3. Efficiency: Good icon's placement
  4. Instant gratification: Fewer steps for quicker access
  5. Aesthetics: Realistic 3D rendering and animation A simple, clean, and streamlined design allows the users to navigate easily, especially those of whom with not much computer experience (see the flow chart below). Each icon clearly represents a particular view for the users to recognize it quickly. The location of icons is designed to accommodate easy access when holding the mobile device (Placement on the left and right allows the users to navigate with ease and comfort). It also needs to allow users to enjoy the main functionalities without having to go through many steps, i.e., login steps. The 3D rendering and animation is essential and may attempt to display images as realistic as possible to allow detailed analysis by the users.

Figure 8D:
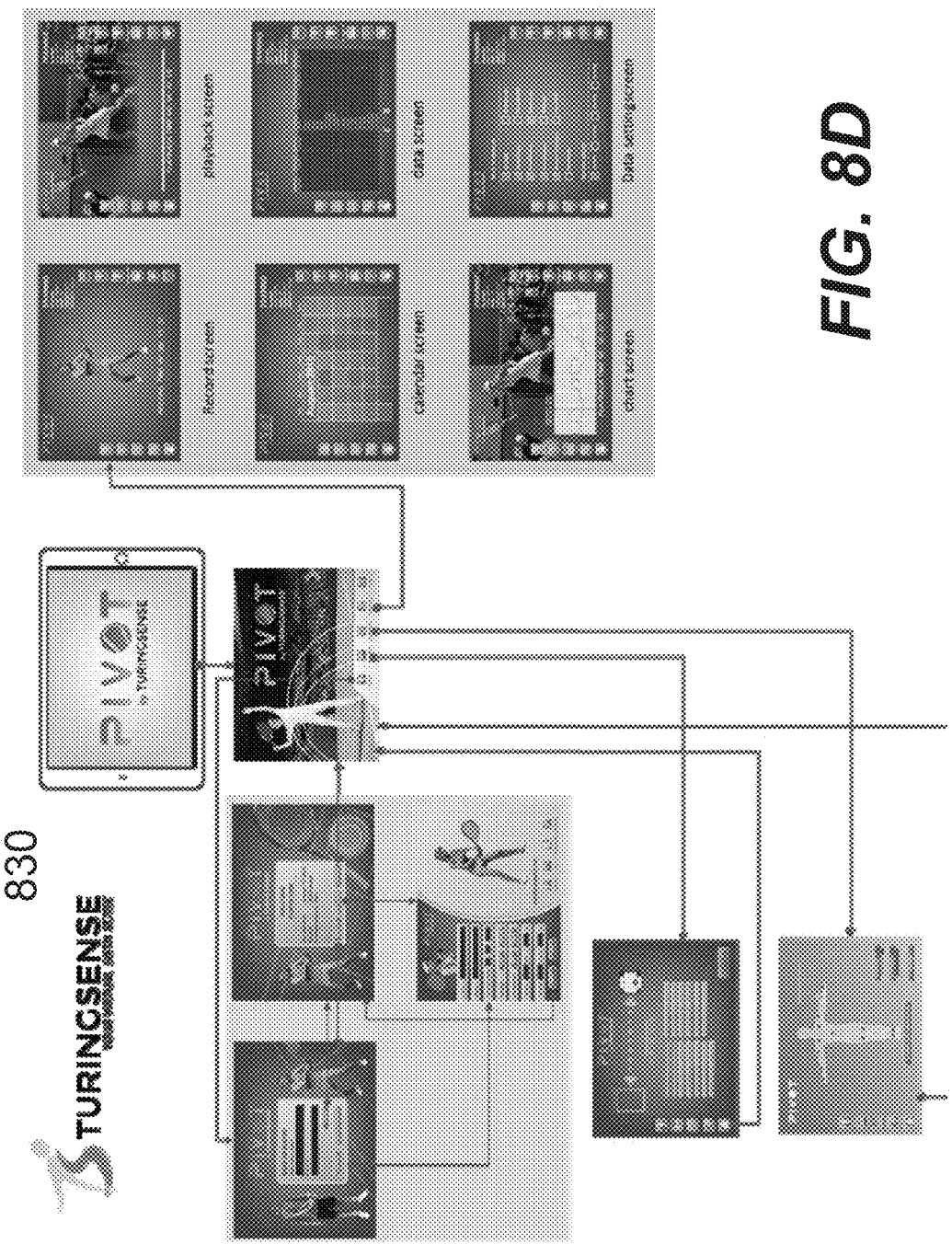
FIG. 8D shows an exemplary user interface for tennis application.

FIG. 8D shows an exemplary user interface (UI) for tennis application. The UI allows the users to access the live animation immediately without having them to go through registration. The goal may be to keep them engaged quickly and curious to know further. There may be Chart, History, Setting, and Back on the left side close to the left thumb for easy access by the left thumb. The right side, for the right thumb, gives access to the 3D manipulation and camera set up.

The embodiments may provide access to a rich database to be analyzed. The richness of the data may overwhelm the users, hence, a simple presentation may be provided via a pivot chart. The x-axis represents the strokes. The y-axis can pivot to different data attributes to be analyzed, i.e., swing speed, vibration, footsteps, elbow flexion/angle, knee angle/bend, balance, etc. The z-axis represents the type of stroke.

Figure 8E:
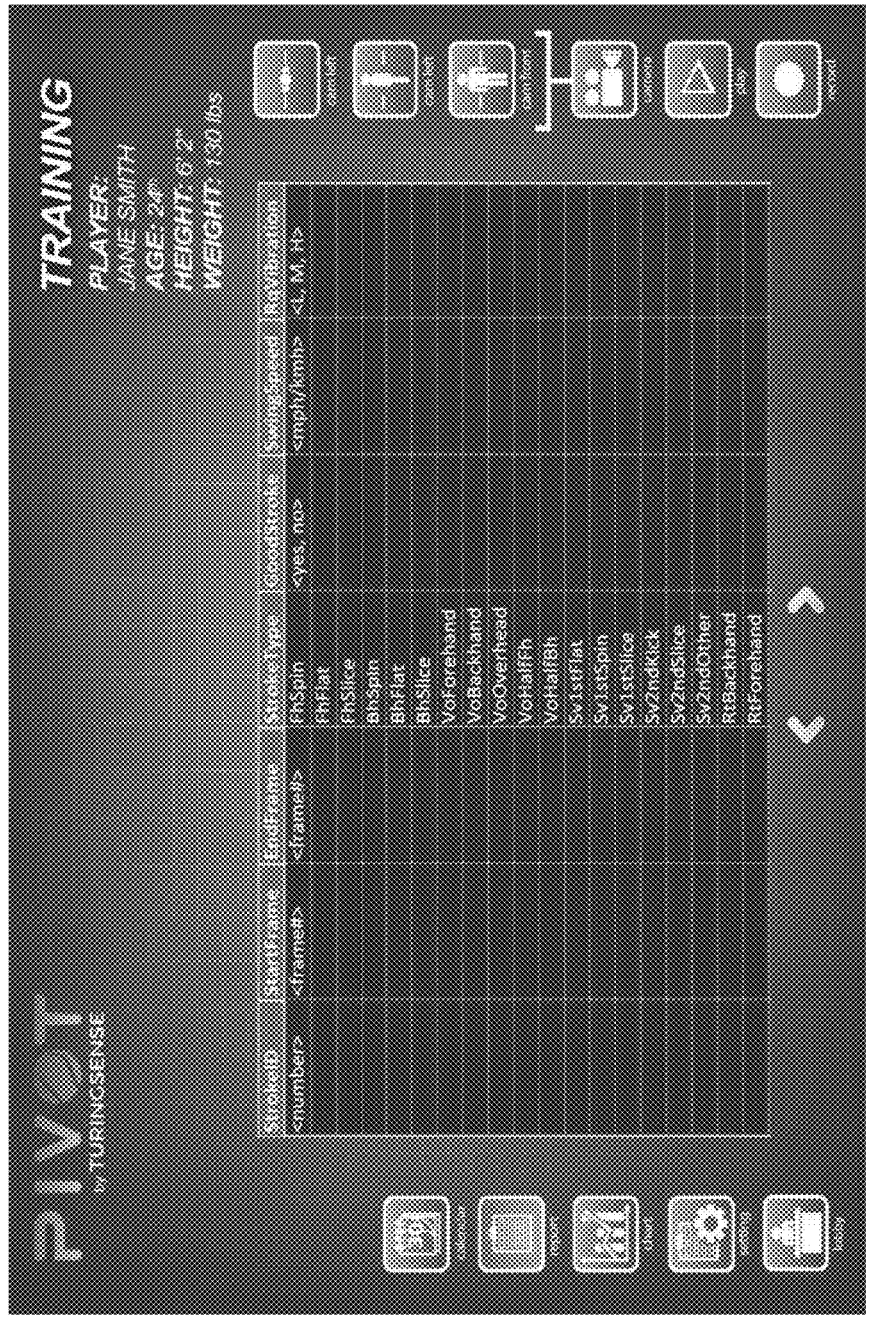
FIG. 8E shows an exemplary pivot chart, where the data can be categorized by the stroke type.

FIG. 8E shows an exemplary pivot chart, where the data can be categorized by the stroke type. The attributes of each stroke are then categorized into color-coded groups when the data is related to each other. Each point in the chart is represented with color-coded tennis ball. The red means good stroke, yellow/orange means better stroke, and green means best stroke. Users can visually recognize the overall performance quickly based on the colors. Zooming in/out of the chart can be done by pinching and spreading with two fingers. Scrolling the chart left and right can be done by swiping with one finger. Tapping each ball will bring the 3D avatar animation, replaying that particular stroke.

Figure 8F:
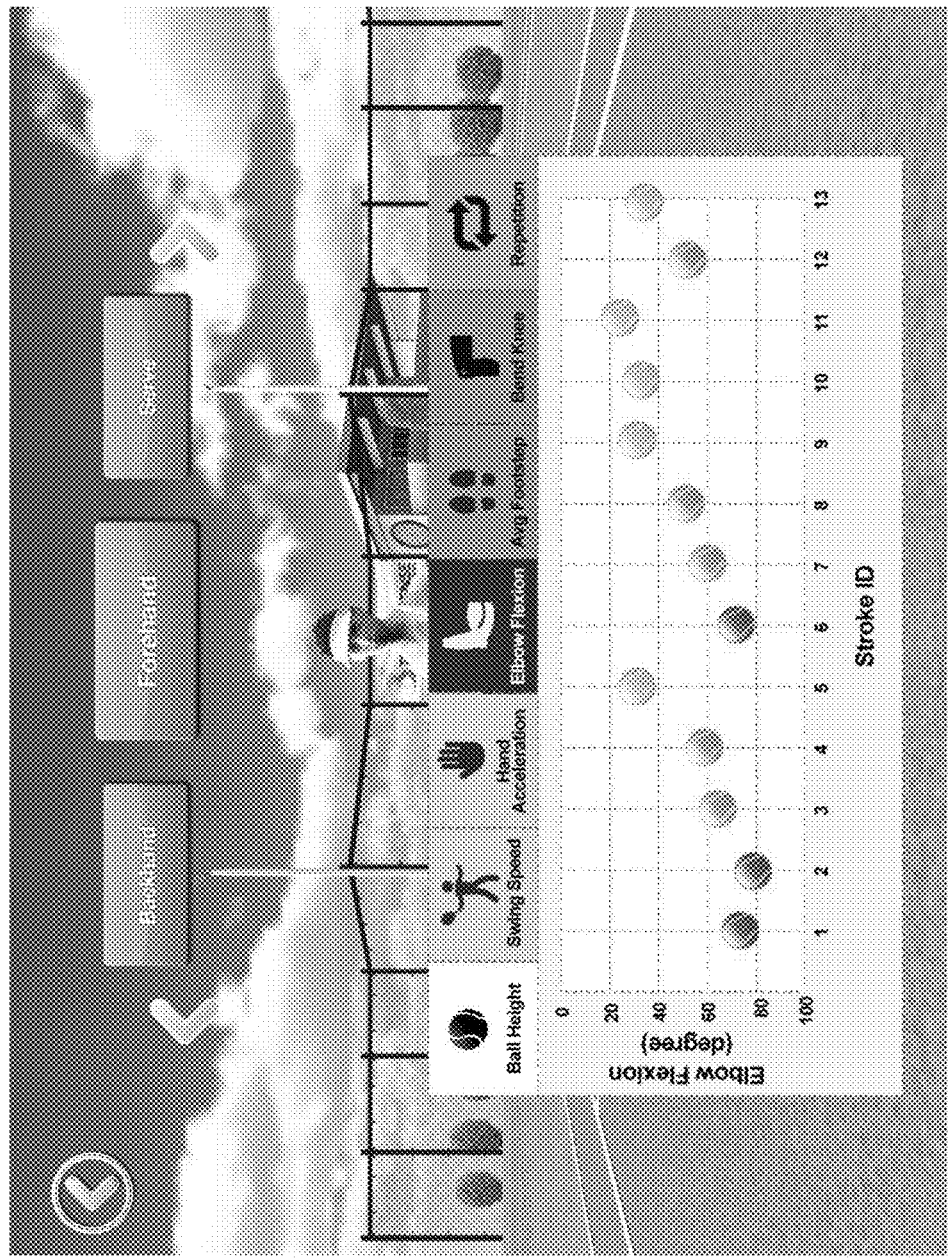
FIG. 8F shows an exemplary history that allows a user to keep track of his training, where each tennis ball represents a training day.
Figure 8G:
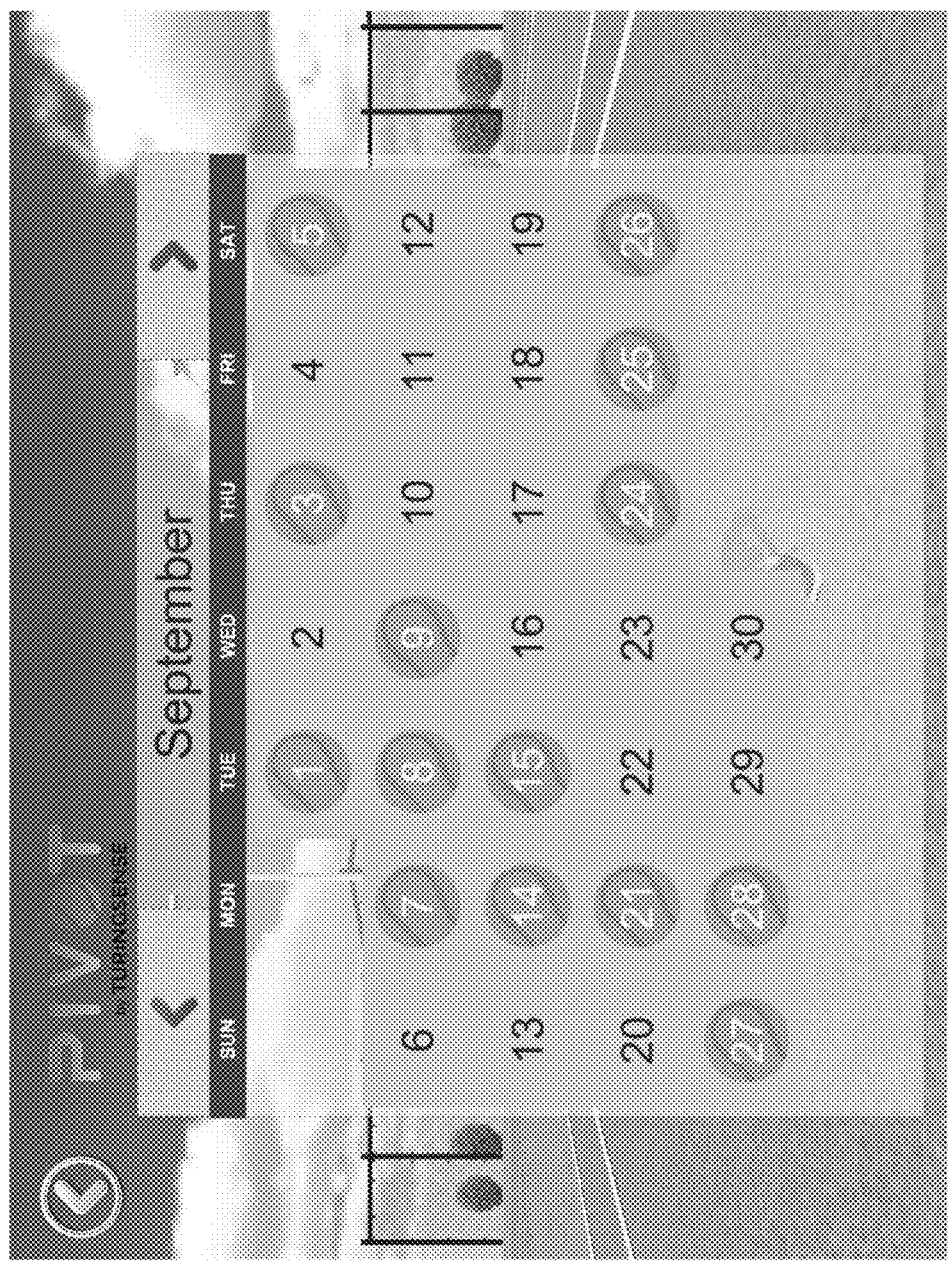
FIG. 8G shows an exemplary background of the UI showing the history that allows a business or an advertiser to buy embedded marketing or product placement for monetization.
Figure 8H:
FIG. 8H shows an example of showing a product placement of TuringSense.

FIG. 8F shows an exemplary history that allows a user to keep track of his training, where each tennis ball represents a training day. The history allows a user or registered users to keep track of their training. According to one embodiment, FIG. 8G shows an exemplary background of the UI showing the history that allows a business or advertiser to buy embedded marketing or product placement for monetization. As shown in FIG. 8H, there is a product placement of TuringSense. As to sensor placement, one embodiment may enable flexible placement sensor on different body segments and various sensor location configurations to achieve a rich set of motion analysis. Each sensor may be programmable to be placed on different body segments, allowing greater flexibility to do motion analysis and motion capture. For example, a sensor for the wrist can also be placed on the ankle. This flexibility allows a small set of sensors (e.g., 5 sensors) to achieve a comprehensive motion analysis. The following table shows an example of sensor placement.

| Attributes | # of sensors | Locations |
| --- | --- | --- |
| Start of motion | 1 | Wrist |
| End of motion | 1 | Wrist |
| Ball contact | 1 | Wrist |
| Racquet height at contact | 5 | Chest, scapula, upper arm, wrist, hand |
| Type of motion | 1 | Wrist |
| Sub-type of motion | 3 | Chest, upper arm, wrist |
| Swing speed | 1 | Wrist |
| Hand acceleration | 1 | Hand |
| Elbow flexion | 3 | Chest, upper arm, wrist |
| Elbow pronation | 3 | Chest, upper arm, wrist |
| Number of steps | 1 | Shank |
| Knee flexion | 3 | Chest, thigh, shank |
| Number of repetition | 1 | Wrist |

All of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located, and may be cloud-based devices that are assigned dynamically to particular tasks. The results of the disclosed methods and tasks may be persistently stored by transforming physical storage devices, such as solid state memory chips and/or magnetic disks, into a different state.

The methods and processes described above may be embodied in, and fully automated via, software code modules executed by one or more general purpose computers. Some or all of the methods may alternatively be embodied in specialized computer hardware. Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed methods may be stored in any type of non-transitory computer data repository, relational databases and flat file systems that use magnetic disk storage and/or solid state RAM. Some or all of the components shown in the figures, such as those that are part of the Customer System, may be implemented in a cloud computing system.

Further, certain implementations of the functionality of the present disclosure are sufficiently mathematically, computationally, or technically complex that application-specific hardware or one or more physical computing devices (utilizing appropriate executable instructions) may be necessary to perform the functionality, for example, due to the volume or complexity of the calculations involved or to provide results substantially in real-time.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the implementations described herein is for illustrative purposes and should not be understood as requiring such separation in all implementations. It should be understood that the described program components, methods, and systems can generally be integrated together in a single computer product or packaged into multiple computer products. Many implementation variations are possible.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network or any other type of communication network.

The present invention has been described in sufficient details with a certain degree of particularity. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the foregoing description of embodiments.

We claim:

1. A method for capturing motion performed by a user, the method comprising:
   receiving in a computing device sensing data wirelessly from a plurality of sensor modules respectively attached to different body parts of the user in accordance with a particular sport;
   deriving the motion of the user per the received sensing data;
   generating a 3D graphic environment pertaining to the sport to compare reference motion performed by a reference chosen by the user with the derived motion performed by the user; and
   highlighting differences in the 3D graphic environment between the reference motion and the derived motion, wherein the differences are animated in the 3D graphic environment.

2. The method as recited in claim 1, wherein said receiving in a computing device sensing data wirelessly from a plurality of sensor modules comprises: the computing device communicating with one of the sensing modules designated as a hub module, wherein the hub module is configured to combine the sensing data generated in each of the sensing modules.

3. The method as recited in claim 1, wherein the user uses a piece of equipment to hit an object in performing the sport, said receiving in a computing device sensing data comprising:
   deriving one or more trajectories of one or more of the different body parts per the sport; and
   deriving coordinates of the object based on the trajectories, wherein the object is assumed to be hit by the equipment.

4. The method as recited in claim 3, further comprising:
   superimposing the object in the 3D graphic environment to show how the object is projecting along a trajectory derived from the trajectories.

5. The method as recited in claim 4, wherein said highlighting differences in the 3D graphic environment between the reference motion and the derived motion comprises:

superimposing the trajectory along with a trajectory of the reference motion.

6. The method as recited in claim 4, wherein the object is a ball.

7. The method as recited in claim 4, wherein the one or more of the different body parts includes chest, shoulder, upper arm, forearm, hand, right and left thigh, right and left shank.

8. The method as recited in claim 1, wherein said deriving the motion of the user per the received sensing data comprises:
determining a body part of the user corresponding to one of the sensor modules as an origin of a two-dimensional plane to create a direct kinematics model.

9. The method as recited in claim 8, wherein the two-dimensional plane is constructed to include a sagittal plane and a frontal plane motion, whereby providing a double 2D model.

10. The method as recited in claim 1, wherein the reference is chosen by the user from a motion library provided to allow the user to perform one of stored reference motions trimmed from recorded motions, select a motion to setup a specific lesson, train on-court with instant audio feedback, select a motion to imitate in a shadow motion game, or share a library with others.

11. A system for capturing motion performed by a user, the system comprising:
a plurality of sensor modules, respectively attached to different body parts of the user, the sensor modules generating sensing data when the user moves in accordance with a particular sport; and
a computing device wirelessly receiving the sensing data to derive the motion of the user per the received sensing data, generate a 3D graphic environment pertaining to the sport to compare reference motion performed by a reference chosen by the user with the derived motion performed by the user, wherein differences between the reference motion and the derived motion are animated in the 3D graphic environment.

12. The system as recited in claim 11, wherein the computing device communicates with one of the sensing modules designated as a hub module, wherein the hub module is configured to combine the sensing data generated in each of the sensing modules.

13. The system as recited in claim 11, wherein the user uses a piece of equipment to hit an object in performing the sport, the computing device is configured to perform operations of:
deriving one or more trajectories of one or more of the different body parts per the sport; and
deriving coordinates of the object based on the trajectories, wherein the object is assumed to be hit by the equipment.

14. The system as recited in claim 13, wherein the computing device is configured to further perform operations of:
superimposing the object in the 3D graphic environment to show how the object is projecting along a trajectory derived from the trajectories.

15. The system as recited in claim 14, wherein the trajectory is superimposed along with a trajectory of the reference motion in the 3D graphic environment.

16. The system as recited in claim 14, wherein the object is a ball.

17. The system as recited in claim 14, wherein the one or more of the different body parts includes chest, shoulder, upper arm, forearm, hand, right and left thigh, right and left shank.

18. The system as recited in claim 11, wherein a body part of the user corresponding to one of the sensor modules is chosen as an origin of a two-dimensional plane to create a direct kinematics model.

19. The system as recited in claim 18, wherein the two-dimensional plane is constructed to include a sagittal plane and a frontal plane motion, whereby providing a double 2D model.

20. The system as recited in claim 11, wherein the reference is chosen by the user from a motion library provided to allow the user to perform one of storing reference motions trimmed from recorded motions, select a motion to setup a specific lesson, train on-court with instant audio feedback, select a motion to imitate in a shadow motion game, or share a library with others.

* * * * *